(12) United States Patent
Dong et al.

(10) Patent No.: US 12,108,719 B2
(45) Date of Patent: *Oct. 8, 2024

(54) METHODS FOR CREATING DOUBLED HAPLOID PLANTS

(71) Applicant: Monsanto Technology LLC, St. Louis, MO (US)

(72) Inventors: Fenggao Dong, St. Louis, MO (US); Michael Graham, St. Louis, MO (US); Huachun Larue, St. Louis, MO (US); Daniel Ovadya, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 124 days.

This patent is subject to a terminal disclaimer.

(21) Appl. No.: 17/218,954

(22) Filed: Mar. 31, 2021

(65) Prior Publication Data

US 2021/0219507 A1    Jul. 22, 2021

Related U.S. Application Data

(63) Continuation of application No. 15/745,236, filed as application No. PCT/US2016/042471 on Jul. 15, 2016, now abandoned.

(60) Provisional application No. 62/193,389, filed on Jul. 16, 2015.

(51) Int. Cl.
| | | |
|---|---|---|
| *A01H 3/04* | (2006.01) | |
| *A01H 1/06* | (2006.01) | |
| *A01H 5/10* | (2018.01) | |
| *A01H 6/46* | (2018.01) | |
| *A01N 43/84* | (2006.01) | |
| *A01H 1/08* | (2006.01) | |

(52) U.S. Cl.
CPC ............ *A01H 3/04* (2013.01); *A01H 1/06* (2013.01); *A01H 5/10* (2013.01); *A01H 6/4684* (2018.05); *A01N 43/84* (2013.01); *A01H 1/08* (2013.01); *A01H 6/4678* (2018.05)

(58) Field of Classification Search
None
See application file for complete search history.

(56) References Cited

U.S. PATENT DOCUMENTS

| | | |
|---|---|---|
| 5,866,513 A | 2/1999 | Michelotti et al. |
| 7,902,437 B1 | 3/2011 | Carrigan |
| 8,742,237 B1 | 6/2014 | Roeber |
| 8,791,047 B2 | 7/2014 | Haas et al. |
| 2008/0216191 A1 | 9/2008 | Barton et al. |
| 2010/0050501 A1 | 3/2010 | Rooney et al. |
| 2010/0169999 A1 | 7/2010 | Cui et al. |
| 2013/0205438 A1 | 8/2013 | Barton et al. |
| 2014/0266196 A1 | 9/2014 | Dai et al. |
| 2014/0310832 A1 | 10/2014 | McIntyre et al. |
| 2019/0014730 A1 | 1/2019 | Dong et al. |

FOREIGN PATENT DOCUMENTS

| | | |
|---|---|---|
| CN | 1843089 A | 10/2006 |
| CN | 102118965 | 7/2011 |
| CN | 102118965 A | 7/2011 |
| EP | 0753257 A1 | 1/1997 |
| WO | 2007038075 A1 | 4/2007 |
| WO | 2014/037947 A1 | 3/2014 |
| WO | 2015/168659 A1 | 11/2015 |
| WO | 2017011737 A1 | 1/2017 |

OTHER PUBLICATIONS

Geiger, H.H. and Gordillo, G.A., Maydica 2009, vol. 54; pp. 485-499. (Year: 2009).*
Xu, N. et al. Plant Growth Regulation, 2004; vol. 44, pp. 231-241. (Year: 2004).*
Bayat et al., "Paclobutrazol and Salicylic Acid Application Ameliorates the Negative Effect of Water Stress on Growth and Yield of Maize Plants", Journal of Research in Agricultural Science, 2012, pp. 127-139, vol. 8, No. 2.
Chalyk et al., "Regular Segregation of Four Recessive Marker Genes Among Maternal Haploids in Maize," Plant Breeding, 2000, pp. 363-364, vol. 119.
Chalyk, "Properties of Maternal Haploid Maize Plants and Potential Application to Maize Breeding," Euphytica, 1994, pp. 13-18, vol. 19.
Chen et al., "Micron traditional Chinese medicine—Study and application of ultrafine powder of traditiona Chinese medicine", China Medical Science and Tech Press, 1st edition, p. 155, Aug. 31, 2007.
Coe, "A Line of Maize With High Haploid Frequency," The American Naturalist, 1959, pp. 381-382, vol. 93, Issue 873.
Deimling et al., "Methodology and Genetics of In Vivo Haploid Induction in Maize," Vort Pflanzenzuchtg, 1997, pp. 203-224, vol. 38.
Espindula et al., "Use of Growth Retardants in Wheat", Plant Daninha, 2009, vol. 27, No. 2, pp. 379-387.
Geiger et al., "Doubled Haploids in Hybrid Maize Breeding", Maydica, 2009, pp. 485-499, vol. 54.
Gomez et al., "Can Yield Potential be Increased by Manipulation of Reproductive Partitioning in Quinoa (Chenopodium quinoa)? Evidence from Gibberellic Acid Synthesis Inhibition Using Paclobutrazol", Functional Plant Biology, 2011, pp. 420-130, vol. 38.
Haiying et al, "Effects of different plant growth regulators on argronomic traits and yields of wheat", Journal of Seed Industry Guide, Nov. 10, 2014 pp. 12-13, No. 11.
Huang et al, "Physiology of wheat cultivation", Shanghai science and technology press, 1st Edition, pp. 71-76, Sep. 30, 1984.

(Continued)

*Primary Examiner* — Russell Kallis
(74) *Attorney, Agent, or Firm* — McBee Moore & Vanik IP, LLC

(57) ABSTRACT

Provided are methods for increasing the efficiency of creating doubled haploid plants by increasing the number of chances of forming a double haploid seed through treatment of a monocot plant with a plant growth regulator. In certain embodiments, maize plants are produced that comprise multiple co-dominant ears. Also provided are plants comprising the potential to generate increased numbers of doubled haploid offspring.

18 Claims, 5 Drawing Sheets

(56) References Cited

OTHER PUBLICATIONS

Kasha et al., "High Frequency Haploid Production in Barley (*Hordeum vulgare* L.)", Nature Publishing Group, Feb. 1970, pp. 874-876, vol. 225.
Li et al., "Morphology and anatomy of gramineae crops" Shanghai Sci. and Tech. Press, 1st Edition, p. 515, Jun. 30, 1979.
Li, et al., "Cultivation of dwarf seedling with polyprazole", Jiangxi Agri. Sci. and Tech., May 1, 1987, pp. 26-27.
Matthys-Rochon et al.,"In Vitro Development of Maize Immature Embryos: A Tool for Embryogenesis Analysis", Journal of Experimental Botany, May 1998, pp. 839-845, vol. 49, No. 322.
Mei et al., "Basic priniciples of wheat production systems engineering", China environmental science press, 1st Edition, p. 68, Nov. 30, 1996.
Mulan et al., "Study on the effects of physiology, stigma activity and cross seed setting of uniconazole on ecological male sterile wheat", http://www.doc88.com/p-6177023255655.html, Aug. 27, 2014.
English Translation of Office Action and Search Report for CN Application 2016800460661, dated Mar. 3, 2020.
Prigge et al., "Production of Haploids and Doubled Haploids in Maize", Plant Cell Culture Protocols, Third Edition, pp. 161-172.
Rethwisch et al., "Comparision of Multiple Rate of Apogee and Palisade for 'Cheyenne' Bermudagrass Seed Production", Forage and Grain: A College of Agriculture and Life Sciences Report, College of Agriculture, Oct. 2004, pp. 59-62; Abstract, p. 60, para 2.
Rober et al., "In Vivo Haploid Induction in Maize—Performance of New Inducers and Significant of Doubled Haploid Lines in Hybrid Breeding", Maydica, 2005, pp. 275-283, vol. 50.
Rolston et al., "Grass Seed Yields Increase with Plant Growth Regulators and Fungicides" Proceeding of the New Zealand Grassland Association 66, 2004, pp. 127-132; Abstract, Table 1-2.
Schluttenhofer et al., "Use of Uniconazole to Control Plant Height for an Industrial/Pharmaceutical Maize Platform", Industrial Crops and Products, 2011, vol. 33, pp. 720-726.
Wang, et al., "Advanced plant physiology", China agricultural university press, 1st Edition, p. 330, Mar. 31, 2013.
Xu et al., "Co-Regulation of Ear Growth and Internode Elongation in Corn", Plant Growth Regulation, 2004, pp. 231-241, vol. 44.
Xu et al., "Paclobutrazol Improved the Reproductive Growth and the Quality of Seed Oil of Jatropha Curcas", Journal of Plant Growth Regulation, 2013, pp. 875-883, vol. 32.
Ye et al., "Modern pesticide application technology book", China Agriculture Press, 1st edition, pp. 456-457, Oct. 31, 2002.
Zhang, Qipeng, "Agricultural technology textbook—Crop cultivation", Dept. of Science and Education, Shanxi agriculture bureau, Shanxi scient and technology press, pp. 74-78, Feb. 28, 1984.
Rethwisch et al. (2004) Forage and Grain: A College of Agriculture and Life Sciences Report 59-62.
"A Brief Explanation of Terms of Agricultural Science and Technology", Information Research Institute of Shandong Academy of Agricultural Sciences, May 1, 1980, p. 5.
English Translation of First Office Action and Search Report for CN2016800433132, dated May 1, 2021.
English Translation of Second Office Action and Search Report for CN2016800460661, dated Dec. 1, 2020.
Yuju et al, "The New Pesticide is Safe and Useful", Zhongyuan Farmers Publishing House, Jun. 30, 2011, pp. 337-338.
Zhi'an, Zhang, "Experimental Techniques in Plant Physiology", Jilin University Press, Jul. 31, 2008, p. 173.

* cited by examiner

METHODS FOR CREATING DOUBLED HAPLOID PLANTS

CROSS-REFERENCE TO RELATED APPLICATIONS

This application is a Continuation of U.S. National Phase patent application Ser. No. 15/745,236, filed Jan. 16, 2018, which claims priority to 35 U.S.C. § 371 U.S. National Phase Application of International Patent Application No. PCT/US2016/042471, filed Jul. 15, 2016, which claims the benefit of U.S. Provisional Patent Application No. 62/193,389, filed on Jul. 16, 2015, all of which are incorporated herein by reference in their entireties.

BACKGROUND

The evolution and domestication of plants has generally followed a common pattern or "domestication syndrome" that distinguishes crops from their wild progenitors. One common domestication syndrome feature among crops arose from long-term selection for increased apical dominance, which is characterized by relatively more robust growth of a central stem and its buds and flowers in comparison to the growth of side stems and axillary buds, which has resulting in fewer and larger fruits per plant. The selection for apical dominance is considered an important symptom of domestication in many species, including the cereal crops of rice, wheat, barley and maize, as well as fruit crops like tomato.

A critical challenge during the domestication of crop plants was to improve the harvestability of the crop as compared to its progenitor. In unfavorable environments, wild plants often flower and mature rapidly; producing smaller numbers of branches, inflorescences, flowers and seeds in order to increase the likelihood of producing at least one offspring to continue the life cycle. In favorable environments, wild plants maximize the probability of successful reproduction by sequentially producing more branches, inflorescences, flowers and seeds over time. The latter strategy is not optimal for a crop as it is more efficient to harvest a fewer but larger fruit or inflorescences that mature synchronously from plant to plant which permits a single harvest at an optimal time of fruit or inflorescence maturation. Thus, diverse crops have been selected to produce smaller numbers of larger seeds, fruits or inflorescences on the main stem as a means of improving harvestability.

Perhaps the most striking and well-studied alteration in plant architecture was brought about by the domestication of maize. By selecting for traits that improve yield and mechanical harvestability, humans have transformed the progenitor of maize from a bushy, shrub-like ancestor with multiple elongated lateral branches tipped by male or female florescences into today's crop comprising a single, erect main stem with only two or three relatively abbreviated lateral branches, each terminating in a single female flower (ear). Today it is generally accepted that selecting for apical dominance in maize not only improves overall yield in ideal growing conditions, but it also makes the logistics of coordinating flowering times among and between lines much easier and streamlines field maintenance and mechanical harvestability.

The mechanism of apical dominance in maize involves the regulation of hormones such as auxin, which is produced by the apical meristem. As the primary ear begins to mature, greater amounts of auxin are produced by the apical meristem. The auxin is carried from the apical meristem down the plant and suppresses development of lower ears, resulting in secondary ears that are less likely to nick well or produce viable seed.

Haploid sporophyte plants contain a gametic chromosome number (n) and can originate spontaneously or through artificial induction. Haploids tend to be less vigorous and less fertile than a sporophyte of similar genotype with the zygotic chromosome number (2n), and so are of limited direct benefit to researchers seeking to improve plant genetics.

Although spontaneous chromosome doubling does occur, the frequency is so low (typically less than 5%), that researchers attempting to create doubled haploids plants ("DH plants") often subject haploid plants to treatments that promote chromosome doubling. Haploid plant seedlings subjected to a chromosome doubling treatment can produce haploid egg and/or sperm, and if these plants are successfully selfed, the zygotic chromosome number can be recovered in the offspring, thus restoring the vigor and fertility expected of a 2n sporophyte.

During chromosome doubling, each homologue is replicated to create a substantially identical copy of the original and thus the entire genome of a DH plant is usually considered homozygous at each locus. This process can create completely homozygous and homogenous lines in fewer generations than traditional backcrossing, thereby improving selection efficacy, reducing the number and length of breeding cycles, and consuming fewer resources.

The likelihood of generating large numbers of doubled haploid offspring from a given haploid plant using methods currently known in the art is so low, however, that it severely reduces the advantages of incorporating them on a large scale in a competitive breeding program. As far back as the 1950s researchers have been attempting to improve doubling rates in plants and have developed techniques for over 250 crop species. However, even the best methods described reliably yield doubling rates of only 12% or less and typically depend on the application of the anti-microtubule drug colchicine, which is toxic to plants at the concentrations required. The effects are also highly genotype specific.

Furthermore, current doubling methods are labor intensive and often require that plants are handled several times during treatment, reducing their survival rate. Haploid plants often become so fragile during colchicine treatment that even if they live through it and are successfully doubled, they do not survive the subsequent handling and downstream processing steps necessary to transplant them to a field, greenhouse, or other growth conditions where they can recover and eventually grow to produce seed. Thus, plant breeders and researchers will typically use a gauge that characterizes both the likelihood that a haploid plant is doubled as well as the likelihood that the plant survives to produce doubled haploid seed when comparing the overall effectiveness of one doubling method to another.

SUMMARY

Provided herein are methods for increasing the number inflorescences a monocot plant produces. In certain embodiments, methods of increasing the number inflorescences a monocot plant produces comprise contacting the monocot plant with a plant growth regulator to produce a greater number of inflorescence than a control plant which was not contacted with the plant growth regulator.

Certain aspects provide for methods of producing co-dominant ears on a maize plant. In certain embodiments, the methods comprise contacting a maize plant with a plant growth regulator, such that the maize plant produces co-dominant ears. In certain embodiments, the maize plant produces at least two co-dominant ears. In certain embodiments, the maize plant produces three, four, five, or more co-dominant ears.

In certain embodiments of any of the methods disclosed herein, the plant can be a haploid plant.

Certain aspects provide for methods of improving the number of $DH_1$ seeds obtained or harvested from a $DH_0$ maize plant. Certain aspects provide for methods of increasing the number of $DH_1$ seeds produced by a $DH_0$ maize plant. Certain aspects provide for methods of producing co-dominant ears on a $DH_0$ maize plant. In certain embodiments, any of such methods comprise contacting a $DH_0$ maize plant with a plant growth regulator at any one of developmental stage V4, V5, V6, V7, V8, V9, or V10 and contacting the $DH_0$ maize plant with a chromosome doubling agent at any stage of its life cycle. In certain embodiments, any of such methods comprise contacting a $DH_0$ maize plant with the chromosome doubling agent at any one of developmental stage V4, V5, V6, V7, V8, V9, or V10. In certain embodiments, such methods produce a $DH_0$ maize plant that produces at least one $DH_1$ maize seed and at least two co-dominant ears. In certain embodiments the total number of $DH_1$ maize seeds produced by the $DH_0$ maize plant with at least two co-dominant ears is greater than the number of $DH_1$ maize seeds produced by control $DH_0$ maize plants that exhibit a single dominant ear. In certain embodiments, the $DH_0$ maize plant produces a first co-dominant ear and a second co-dominant ear and the second co-dominant ear produces more $DH_1$ maize seeds than the first co-dominant ear. In certain embodiments, the $DH_0$ maize plant produces a first co-dominant ear, a second co-dominant ear, and a third co-dominant ear, and the third co-dominant ear produces more $DH_1$ maize seeds than the first co-dominant ear. In certain embodiments, the methods further comprise genotyping the $DH_0$ maize plant prior to contacting the $DH_0$ maize plant with the plant growth regulator or the chromosome doubling agent. This can be used to allow for information about the $DH_0$ maize plant to be used to select which $DH_0$ maize plant or plants to contact or in what manner to contact them to achieve desired results. In certain embodiments, the methods further comprise obtaining $DH_1$ maize seeds from the $DH_0$ maize plant. In certain embodiments, the methods further comprise genotyping the $DH_1$ maize seeds obtained from the $DH_0$ maize plant or genotyping a plant grown from the $DH_1$ maize seeds. Information about the $DH_1$ maize seeds or plants can be used to decide which seed(s) or plant(s) to carry forward in a breeding program. Thus, in certain embodiments, the methods further comprise growing a $DH_1$ maize seed selected based on the genotyping. In certain embodiments, the methods further comprise crossing a $DH_1$ maize plant grown from selected seed with another plant. In certain embodiments, any of such methods result in a $DE_4$ doubling efficiency of at least about 15%, results in a $DE_{20}$ doubling efficiency of at least about 15%, results in a $DE_{30}$ doubling efficiency of at least about 15%, and/or results in a $DE_{50}$ doubling efficiency of at least about 15%.

In certain embodiments of any of the methods herein, a plant is contacted with the plant growth regulator by drenching, gassing, injecting, or spraying. In certain embodiments, the plant growth regulator is a plant hormone, gibberellic acid inhibitor, cytokinin, or any combination thereof. In certain embodiments, the plant growth regulator is a gibberellic acid inhibitor that is selected from the group comprising chlormequat-CL, mepiquat-CL, AMO-1618, clorphonium-Cl, tetcylacis, ancymidol, flurprimidol, paclobutrazol, uniconazole-P, inabenfide, prohexadione-CA, trinexapac-ethyl, daminozide, exo-16,17-, and dihydro-GA5-13-acetate.

In certain embodiments, the $DH_0$ maize plant is contacted with a chromosome doubling agent, such as colchicine, before it is contacted with the plant growth regulator. In certain other embodiments, the $DH_0$ maize plant is contacted with a chromosome doubling agent after it is contacted with the plant growth regulator. In certain embodiments, the $DH_0$ maize plant is contacted with the chromosome doubling agent within 1 minute, 5 minutes, 15 minutes, 30 minutes, 1 hour, 2 hours, 3 hours, 6 hours, 12 hours, or 24 hours before or after contact with the plant growth regulator. In certain embodiments, the chromosome doubling agent and the plant growth regulator are contacted with the $DH_0$ maize plant at the same time.

In certain embodiments, a maize plant is contacted with the plant growth regulator at developmental stage V4, V5, or V6. In certain embodiments, a maize plant is contacted with the plant growth regulator at developmental stage V6, V7, V8, V9, or V10.

In certain embodiments, the method results in three or more, four or more, or five or more co-dominant ears produced on a single maize plant. Certain embodiments provide for an elite haploid maize plant comprising at least two co-dominant ears. In certain embodiments, at least one of the co-dominant ears comprises a doubled haploid embryo. Certain embodiments provide for a $DH_0$ maize plant comprising at least two co-dominant ears, wherein at least one of the co-dominant ears comprises a doubled haploid embryo. Certain embodiments provide a maize plant produced by any of the methods described herein.

DETAILED DESCRIPTION

Figure 1:
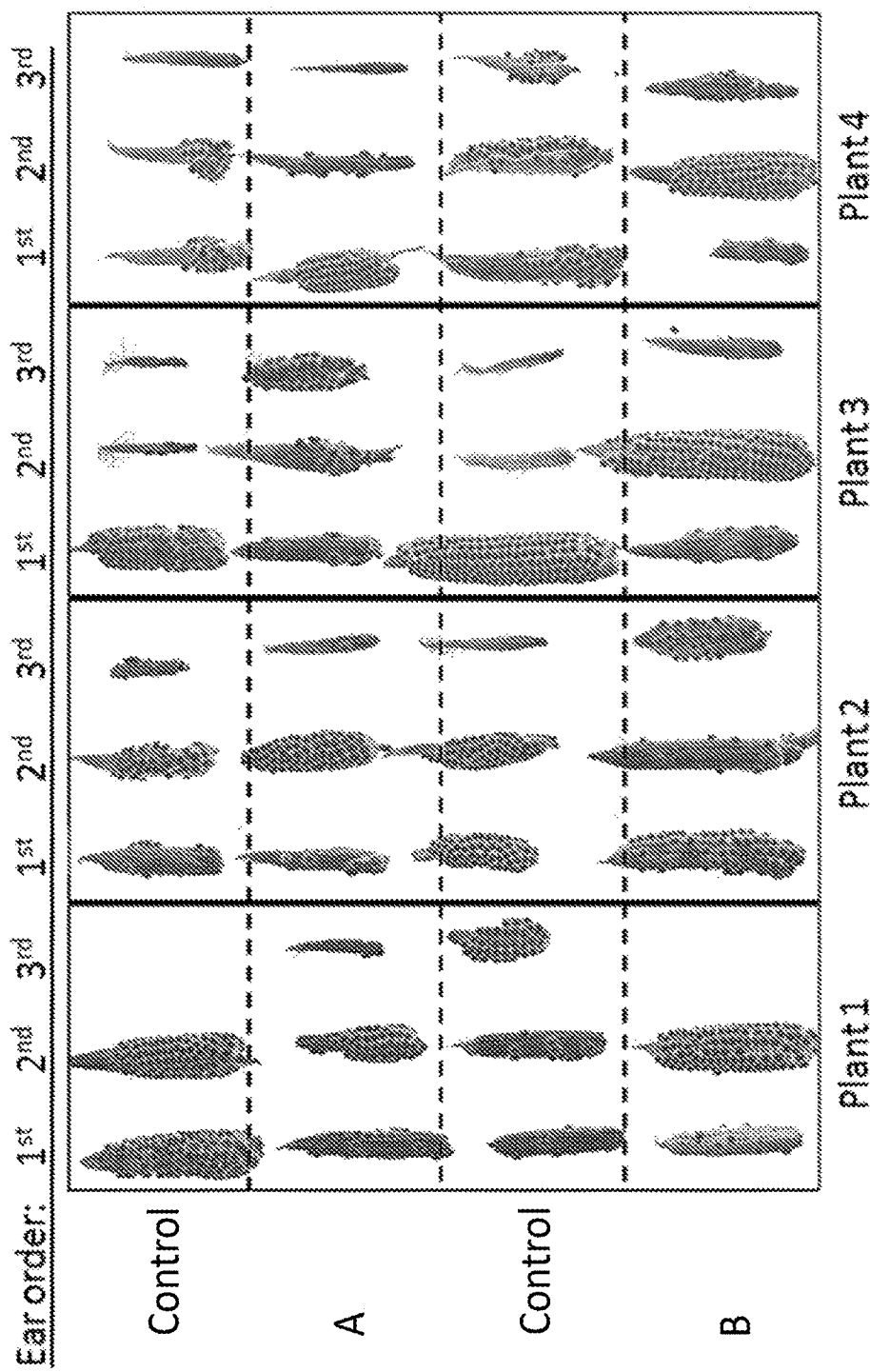
FIG. 1 shows ears classified by their population pedigree, position on the maize stalk, and number of $DH_1$ seed they produced.

Provided herein are methods of inducing or promoting the development of axillary meristems or additional side shoots or additional inflorescences in a crop plant. In certain aspects, this is done for the purpose of improving the efficiency of doubled haploid ("DH") plant production.

It is to be noted that the term "a" or "an" entity refers to one or more of that entity; for example, "a plant," is understood to represent one or more plants. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. Units, prefixes, and symbols are denoted in their Système International de Unites (SI) accepted form. Numeric ranges are inclusive of the numbers defining the range.

The headings provided herein are solely for ease of reference and are not limitations of the various aspects or aspects of the disclosure, which can be had by reference to the specification as a whole. Accordingly, the terms defined immediately below are more fully defined by reference to the specification in its entirety.

Definitions

A used herein, a "plant" refers to a whole monocot plant, any part thereof, or a cell or tissue culture derived from a monocot plant, comprising any of: whole plants, plant components or organs (e.g., leaves, stems, roots, etc), plant tissues, seeds, plant cells, and/or progeny of the same. A plant cell is a biological cell of a plant, taken from a monocot plant or derived through culture from a cell taken from a monocot plant.

As used herein, a "population of plants" or "plant population" refers to a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

As used herein, the term "genetic element" refers to either a recombinant DNA construct (commonly referred to as a "transgene") that has been inserted into the maize genome, a nucleotide sequence, or a genetic locus of a plant genome.

As use herein, the terms "promoting" and "inducing" are used interchangeably to mean either promoting, for example, the development of axillary buds from preexisting buds and inducing, for example, the formation of axillary buds de novo.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the terms "flower" and "inflorescence" are used interchangeably.

As used herein, the terms "maize" and "corn" are used interchangeably.

As used herein, the term "elite," "elite plant," and the like describes a group, germplasm, or population of at least one crop plant that has resulted from human-directed breeding and selection for superior agronomic performance. An "elite population" is an assortment of elite individuals or lines that can be used to represent the state of the art in terms of agronomically superior genotypes of a given crop species, such as maize. Similarly, an "elite germplasm" or "elite strain of germplasm" is an agronomically superior germplasm, typically derived from and/or capable of giving rise to a plant with superior agronomic performance, such as an existing or newly developed elite line of maize. In contrast, an "exotic plant," "exotic line," or "exotic germplasm" is a plant, line, or germplasm derived from a plant not belonging to an available elite line or strain of germplasm. In the context of a cross between two plants or lines of germplasm, an exotic germplasm is not closely related by descent to the elite germplasm with which it is crossed. Most commonly, the exotic germplasm is not derived from any known elite line of a crop, but rather is selected to introduce genetic elements (typically desired alleles) into a breeding program.

Maize plants tend to produce a single dominate, or primary, ear that develops fastest and most completely. Additional ears sometimes form lower down the stalk from the dominant ear (the secondary ear is the next ear down from the primary ear, the tertiary ear next lowest, and so on—all of which can be referred to collectively as secondary ears), but their development is typically delayed with respect to the dominant ear. Because the development of additional, or non-dominant, ears is usually delayed, the dominant ear is typically the only one that nicks well.

As used herein, the term "co-dominant ear(s)" refers to ears on a maize plant that mature at a similar rate/time such that they produce silks receptive to pollen germination in an overlapping timeframe. A plant with co-dominant ears will have at least two co-dominant ears. Co-dominant ears can be numbered by their position on the stalk, i.e., the top co-dominant ear is the first co-dominant ear, the next co-dominant ear down from the first is the second co-dominant ear, the third co-dominant ear is the next lowest, and so on.

As used herein, a control plant (e.g., monocot control plant, maize control plant, etc.), is a plant (or population of plants) recognized as having a representative phenotype (e.g., number of inflorescences, number of tillers, number of ears, number of kernels/seeds, height, biomass, and the like), of a plant that has not been treated with a plant growth regulator but that is in other respects such as genetic makeup and growing conditions comparable to a plant treated with a plant growth regulator. For example, one of ordinary skill in the art would understand a control plant to have one or more of the following attributes: results from a seed derived from the same induction cross; has at least one parent in common with the treated plant; shares a common ancestor with the treated plant within twelve generations; shares sufficient common genetic heritage with the treated plant that one of ordinary skill in the art of plant breeding would recognize the control plant as a valid comparison for establishing a correlation between the application of a plant growth regulator and the resulting phenotype; and/or has one dominant ear and no co-dominant ears (maize). One of ordinary skill in the art will recognize that an untreated plant that by chance (e.g., a statistical outlier), by some other type of manipulation, or other reason comprises a phenotype that varies from a representative phenotype for the untreated plant would not be an appropriate control plant.

Doubling Efficiencies

Haploid plants subjected to a chromosome doubling treatment (or in certain embodiments haploid plants to be subjected to a chromosome doubling treatment) termed $DH_0$ plants, by contact with the chromosome doubling agent can produce haploid egg and/or sperm, and if the $DH_0$ plants are successfully selfed, the zygotic chromosome number can be recovered in the offspring (termed $DH_1$ seeds, plants, etc.), thus restoring the vigor and fertility expected of a 2n sporophyte. "Doubling Efficiency" (DE) is an overall gauge of doubling success calculated by dividing the number of $DH_0$ plants of a designation that produce $DH_1$ seed by the total number of $DH_0$ plants of that designation that were subjected to a chromosome doubling treatment.

While recovery of a single $DH_1$ seed can technically be counted as a successful doubling event, plant breeders usually require a population of at least several plants in order to generate the statistical power necessary to draw confident conclusions from genetic and statistical tests performed on the population. For example, a doubling treatment that produces only one or a few $DH_1$ seeds will be of limited use in a competitive breeding program because at least one additional generation of planting, growing, pollinating, and harvesting will be required to generate a sufficient population size for accurate statistical testing, especially if comparisons across multiple environments are planned. In a relatively large breeding program this seed "bulking" step can push testing of that population back an entire season, which typically delays release of a commercial product, potentially resulting in loss of valuable market share. Since the methods described herein can increase the number of $DH_1$ seeds produced by a $DH_0$ plant in a single generation, they can also reduce the likelihood that an additional generation will be necessary order to bulk up (increase) the number of $DH_1$ seeds from a given cross in order to advance that population onto subsequent steps (e.g. field testing) in a breeding pipeline. Thus, a user of methods described herein will be able to develop improved germplasm for market faster than those using current methods described elsewhere.

In order to better quantify doubling treatment efficacy, minimum yield constraints can be applied during the process of calculating DE such that a given $DH_0$ plant must produce at least a minimum number of $DH_1$ seeds before it is counted in the proportion of successful doubling events, i.e. used in the numerator. Subscripts can be used to signify the minimum yield constraint such that $DE_{20}$ is the doubling efficiency calculated when only $DH_0$ plants that produced at least 20 $DH_1$ seeds are divided by the total number of $DH_0$ plants subjected to the doubling treatment. $DE_{30}$ represents the DE when only the $DH_0$ plants that produced at least 30 $DH_1$ seeds are divided by the total number of $DH_0$ plants subjected to the doubling treatment. Similarly, $DE_{50}$ represents the DE when only the $DH_0$ plants that produced at least 50 $DH_1$ seeds are divided by the total number of $DH_0$ plants subjected to the doubling treatment and so on.

Axillary Bud Induction and Promotion

Described herein is the discovery that it is now possible to dramatically increase the likelihood of recovering a target number of seeds in a single generation from a $DH_0$ monocot plant. Methods comprise inducing or promoting the monocot plant to develop at least one of a variety of different types of axillary buds that can give rise to additional inflorescences. Different embodiments of axillary bud induction and/or treating plants at different growth stages to control the type of axillary bud(s) that develop are possible. Non-limiting examples include multibuds, tillers, and co-dominant ears, which are defined in detail herein.

Axillary bud induction in monocots relaxes the apical dominance that normally inhibits the development of side shoots and/or secondary flowers or inflorescences. In certain embodiments a user causes a mother plant to produce a greater number of fertile female inflorescence and fertile female eggs than current methods of plant breeding and crop cultivation which focus on maximizing the development of a single female inflorescence.

Although known to sometimes arise and develop spontaneously, the formation or development of axillary buds in maize is presently an undesirable trait that is eliminated from breeding programs for a number of reasons described herein. Among these is the idea that hormones responsible for maintaining apical dominance will suppress the development of axillary bud flowers, so it is more efficient if the plant does not waste resources developing them or the vegetative structures that support them. This is especially apparent in modern maize hybrids, where yields are typically maximized in good environments by growing hybrids selected to focus their resources on developing a single, super-performing ear that nicks well and minimize the development of any axillary buds or secondary inflorescences.

It has been discovered, however, that by subjecting a monocot plant to at least one of several possible axillary bud induction treatments at one or more of many possible points in the plant's life cycle it is possible to release the developmental programming for greater apical dominance that plant breeders have selected for. In certain embodiments, a user subjects a monocot plant to a treatment that promotes the development of at least one pre-existing or primordial axillary bud such that it either forms a lateral side shoot (e.g. a tiller) or a secondary (or tertiary, or quaternary, etc.) inflorescence on the main stem of a maize plant. A user can sync the development of at least one axillary bud on a maize plant with the development of other buds on the maize plant to effect a simultaneous and coordinated development of at least two ears on the plant that exhibit the traits expected of a dominant ear, including being receptive to pollination at about the same time (e.g. co-dominant ears). Descriptions and examples herein enable a user to chooses and/or develop an appropriate combination of induction treatment parameters from a wide range of options to suit specific needs. Certain embodiments include subjecting a plant to a treatment that resets the developmental program of at least one cell in the nodal region of the main stem such that it gives rise to at least one new lateral shoot meristem that develops into a new lateral branch capable of producing fertile inflorescences (e.g. multibuds).

Thus, in certain embodiments, a user can confidently recover a target number of seed from a $DH_0$ monocot plant by inducing it to form additional flowers from axillary buds, pollinating those flowers, and then harvesting the seed that form from those additional flowers until the target number of seeds is obtained. By combining all the seeds produced by a plant induced to form additional axillary buds one can increase the chances of producing a desired number of seeds from a single mother plant in a single generation.

Nick

In maize, successful kernel formation requires an overlap in timeframe when the female structures necessary to support fertilization are fully functional and the timeframe when pollen is viable and released from the tassel. Good nick describes circumstances when the overlap in those timeframes is sufficient to fertilize most, if not all, of the available ovaries on the ear. Because pollen can be sensitive to desiccation, heat, and other environmental factors, the timeframe for good nick is often limited to several days or even a few hours. If pollen is released too soon such that most or all of it is non-viable by the time the female flowers are receptive to pollination, then nick will be poor, leading to many unfertilized eggs and poor seed set. Nick is also expected to be poor when pollen is released so late that the silks are dead or the female flowers are otherwise no longer receptive and/or capable of supporting fertilization. Under normal growth conditions the development of secondary ears is usually suppressed and delayed so that the primary ear is typically the only whose development is sufficiently aligned with that of the tassel for good nick to occur.

Nick serves such a crucial connection in the maize life cycle that commercial producers and maize breeders alike spend considerable resources helping ensure it. It is not uncommon for a competitive or industrial breeding program to cull lines otherwise exhibiting excellent performance but do not nick well and thus their maintenance becomes uneconomical. For example, a population of $DH_0$ plants may exhibit a very high rate of doubling and contain excellent genetics, but may still be eliminated from further development if it nicks so poorly that it is a struggle to produce sufficient seed to self and/or maintain or if more than one generation is required to produce sufficient seed for performance testing.

Plant Treatment Agents

In certain embodiments provided herein, a plant can be contacted with a wide variety of "plant treatment agents." Thus, as used herein, a "plant treatment agent", or "treatment agent", or "agent" can refer to any exogenously-provided compound that can be introduced to the surface of a plant and migrate into a plant tissue. In some embodiments, the plant treatment agent acts extracellularly within the plant tissue, such as interacting with receptors on the outer cell surface. In some embodiments, the plant treatment agent enters into cells within the tissue. In some embodiments, the plant treatment agent is contained within a liquid. Such liquids include, but are not limited to, solutions, suspensions, emulsions, and colloidal dispersions.

Contacting a plant with a treatment agent can occur before, during, or after the application of other substances. In certain embodiments, contact between the plant and the treatment agent is achieved by dipping, submerging, or otherwise inserting the plant into a reservoir of liquid comprising the plant treatment agent. Other methods of contacting a plant with a treatment agent include spraying or misting the plant with a solution comprising a plant treatment agent or agitating or tumbling a plant in a solution comprising a plant treatment agent. In certain embodiments, contact between the plant and the treatment agent is achieved by a soil drench, which comprises adding a liquid treatment agent to the soil or growth medium near the roots where the plant will grow.

In certain embodiments, liquids are of an aqueous nature. In certain embodiments, aqueous liquids can comprise water soluble components. In certain embodiments, aqueous liquids can comprise water insoluble components, can comprise an insoluble component that is made soluble in water by addition of a surfactant, or can comprise any combination of soluble components, insoluble components, and surfactants.

A "plant treatment solution" or "treatment solution" can refer to any solution of liquid that comprises a plant treatment agent. In certain embodiments, a plant treatment solution comprises a plant treatment agent and the two terms can often be used synonymously. For example, delivering a plant treatment solution comprising the plant treatment agent colchicine to a plant meristem is essentially synonymous with delivering a plant treatment agent comprising colchicine to a plant meristem.

Plant treatment agents include, but are not limited to, macromolecules including polynucleotides including nucleic acids (e.g. DNA and/or RNA), polypeptides, polysaccharides, polyketides, and the like. Polynucleotides can be single-stranded or double-stranded and can include antisense molecules and interfering RNAs.

Polynucleotides can include mutations and/or various other modifications, such as to their backbones, that are well known in the art. Polynucleotides include "genetic elements", which comprise recombinant DNA constructs (commonly referred to as "transgenes") that have been inserted into a plant genome, or a nucleotide sequence, or a genetic locus of a plant genome. Thus, in certain embodiments, a user of this invention can deliver a sequence of DNA or RNA to a targeted tissue to alter the expression or inheritance of a plant trait, for example, to effectively "transform" a plant by inserting a genetic element into its genome.

Plant treatment agents can also comprise various phytohormones, phytohormone agonists, phytohormone antagonists, or agents that stimulate or inhibit phytohormone perception, signaling or synthesis. In certain embodiments, a plant treatment agent comprises a plant growth regulator (PGR). PGRs are a class of compounds that affect the cellular processes, growth, development or behavior of a plant or plant part. In some embodiments a PGR is responsible for accelerating or retarding the rate of growth or maturation or otherwise altering the behavior of a plant or plant part. In some embodiments, a PGR is a naturally-occurring plant hormone. In some embodiments, a PGR is an chemical alters flowering, internode length, apical dominance, ripening, root architecture, or fruiting, including any substance that affects growth, development, behavior, or reproduction in a monocot plant. Plant growth regulators include auxins (e.g. IAA) and auxin inhibitors, cytokinins (e.g. BAP) and cytokinin inhibitors, compounds that can stimulate ethylene production (i.e. ACC and the like) and compounds that can inhibit ethylene production (AVG and the like), and compounds that inhibit ethylene perception (silver and the like). Plant growth regulators also comprise compounds that modulate plant perception, signaling, and/or behavior, such as giberrellins and their inhibitors (e.g. Paclobutrazol (PBZ) or uniconazole), abscisic acid and its inhibitors, and jasmonic acid and its inhibitors. Other examples include peptide hormones, for example, systemin, phytosulfokine, rapid alkalinization factor and the like.

IAA is indole-3-acetic acid, and IBA is inodole-3-butyric acid. Both are naturally-occurring forms of a class of plant hormones called auxins. Other variations of auxin can be used, including synthetic auxins, such as 2,4-D (2,4-Dichlorophenoxyactic acid and α-NAA (α-Naphthalene acetic acid).

As used herein, PBZ is paclobutrazol, (2S,3S)-1-(4-chlorophenyl)-4,4-dimethyl-2-(1,2,4-triazol-1-yl) pentan-3-ol, also written as $C15H10CIN30$, a plant growth regulator and triazole fungicide. It is a known antagonist of the plant hormone gibberellins that inhibits giberellin biosynthesis, reducing internodal growth and increasing stem girth. BAP is 6-Benzylaminopurine, N-(Phenylmethyl)-7H-pruin-6-amine, also written as C12H11N5. IAA is indole-3-acetic acid, and IBA is inodole-3-butyric acid. Both are naturally-occurring forms of a class of plant hormones called auxins. Other variations of auxin can be used with this invention, including synthetic auxins, such as 2,4-D (2,4-Dichlorophenoxyactic acid) and 1-NAA (1-Naphthalene acetic acid).

As used herein, uniconazole is (e)-(+/−)-beta-((4-chloro-phenyl)methylene)-alpha-(1,1-dimethylethyl)-1h-1,2,4-triazole-1-ethanol, also written as C15H18ClN3O, also known as uniconazole-P. It is a triazole-type plant growth retardant and known antagonist of the plant hormone giberellin that reduces internodal growth and increases stem girth.

In general, plant treatment agents used herein will be water soluble agents. However, the use of plant treatment agents with high, intermediate, low or negligible water solubility can, in certain embodiments, be facilitated by the use of liquid compositions that also comprise various transfer or conditioning agents. Transfer or conditioning agents can comprise any agent that facilitates migration of plant treatment agents to the plant (e.g., plant cells) and/or that facilitate uptake of plant treatment agents by the plant. Transfer or conditioning agents include, but are not limited to, (a) surfactants, (b) an organic solvents or an aqueous solutions or aqueous mixtures of organic solvents, (c) oxidizing agents, (d) acids, (e) bases, (f) oils, (g) enzymes, or combinations thereof. In certain embodiments, methods can optionally include an incubation step, a neutralization step (e. g., to neutralize an acid, base, or oxidizing agent, or to inactivate an enzyme), a rinsing step, or combinations thereof whereby the liquid and plant treatment agent contained therein is treated either before or after delivery to the plant. Transfer or conditioning agents thus include, but are not limited to, emulsions, reverse emulsions, liposomes, and other micellar-like compositions. Examples of useful adjuvants include surfactants and effective molecules contained therein, which include sodium or lithium salts of fatty acids (such as tallow or tallowamines or phospholipids). Transfer or conditioning agents can comprise salts including, but not limited to, sodium, ammonium, calcium, lithium, magnesium, chloride, sulfide, and sulfate salts. Certain embodiments of the methods provided herein use counter-ions or other molecules that are known to associate with plant treatment agents. For certain negatively charged plant treatment agents such as polynucleotides, cations such as inorganic ammonium ions, alkyl ammonium ions, lithium ions, polyamines such as spermine, spermidine, or putrescine, and the like can be used. Organic solvents useful in conditioning a plant cell to permeation with certain plant treatment agents including, but not limited to polynucleotides, are solvents such as DMSO, DMF, pyridine, N-pyrrolidine, hexamethyiphosphoramide, acetonitrile, dioxane, polypropylene glycol, or other solvents that are miscible with water. Naturally derived or synthetic oils with or without surfactants or emulsifiers can be used, e. g., plant-sourced oils, crop oils (such as those listed in the 9th Compendium of Herbicide Adjuvants, publicly available on the world wide web (internet) at "herbicide.adjuvants.com") can be used. Oils useful in certain liquid compositions used in the methods provided herein include, but are not limited to, paraffinic oils, polyol fatty acid esters, or oils with short-chain molecules modified with amides or polyamines such as polyethyleneimine or N-pyrrolidine.

In certain embodiments, a plant treatment agent can be a chromosomal doubling agent. Chromosome doubling agents are used to generate doubled haploid plant cells and doubled haploid plants. Chromosomal doubling agents can comprise various mitotic inhibitors that cause chromosome doubling. In certain embodiments, the chromosome doubling agent can be a compound such as colchicine, amiprophos methyl, trifluralin, oryzalin, pronamide, or chloropropham. In still other embodiments, the chromosome doubling agent can be a low mammalian toxicity chromosomal doubling agent. Various low mammalian toxicity chromosome doubling agents that can be used include, but are not limited to, compounds such as: i) 1,2,3-trimethoxy-4-((1S,6R)-6-nitro-cyclohex-3-enyl)-benzene and other related compounds disclosed in US Patent Application Publication 2010/0169999; and ii) compounds disclosed in U.S. Pat. No. 5,866,513 to Michelotti et al. U.S. Patent Application Publication 2010/0169999 and U.S. Pat. No. 5,866,513 are incorporated herein by reference in their entireties. In particular, the 76 compounds disclosed in Table I and 1a on Cols. 3-4, 5-6, and 7-8 of U.S. Pat. No. 5,866,513 are each incorporated herein by reference. In certain embodiments, the chromosome doubling agent is a polynucleotide.

In certain embodiments, a broad range of chemical concentrations and dosing schedules can be used in conjunction with these methods and one of ordinary skill in the art can optimize the dose administered to a given genotype in order to maximize co-dominant ear formation and/or maximize nicking and/or fertilization among co-dominant ears.

Types of Plants

Unless otherwise specified, this disclosure is not limited to any particular type of monocot plant. For example, in certain embodiments, the monocot plant is a member of the family Poaceae, wheat plant, maize plant, sweet corn plant, rice plant, wild rice plant, barley plant, rye, millet plant, sorghum plant, sugar cane plant, turfgrass plant, bamboo plant, oat plant, brome-grass plant, *Miscanthus* plant, pampas grass plant, switchgrass (*Panicum*) plant, and/or teosinte plant, or is a member of the family Alliaceae, onion plant, leek plant, garlic plant.

Unless otherwise specified, as used herein, a plant may be any whole monocot plant, or part of a monocot plant, or tissue culture derived from a monocot plant, or monocot plant seed; having a tissue to which a plant treatment agent can be delivered. A plant may be of various chromosomal content, such as haploid, diploid, triploid, tetraploid, etc. Polyploidy refers generally to a condition of having a ploidy level greater than triploid. In certain embodiments, a distinction is made between plant tissues grown in tissue culture and non-tissue culture plants.

Unless otherwise specified, as used herein, the surface of a plant refers to the surface that is generally exposed to the external environment surrounding the plant without pulling, cutting, etc. the plant to expose additional areas. For example, if a plant is submerged completely in a solution, the surface of the plant is generally the portion of the plant that would come in contact with the solution.

A plant tissue can be any plant tissue. In certain embodiments, a plant tissue can include a functional meristem or grouping of cells capable of forming a functional meristem. A functional meristem is defined as a center of pluripotent cells that has the ability to give rise to new plant tissues or organs. In certain embodiments, the plant tissue comprises a meristem tissue such as a root apical meristem or a shoot apical meristem.

In certain embodiments, a plant treatment agent is delivered to a targeted or selected plant tissue. A plant tissue can be targeted or selected based on the tissue's response to the plant treatment agent and/or the influence over the plants growth, characteristics, genetics, yield, etc., that is sought to be achieved. For example, the shoot apical meristem, particularly of a $DH_0$ plant, can be selected for the delivery of a chromosome doubling agent. The selected tissue can be located at the surface of the plant and/or it can be located beneath the plant surface or beneath a portion of the plant surface. Thus, in certain embodiments, wherein even the entire surface of a plant is contacted by a solution comprising a plant treatment agent such as by completely submerging the plant, at least a portion of the selected tissue may not be contacted by the solution.

In certain embodiments, prior to germination, the plant or a propagule of the plant is contacted with a plant treatment agent in order to deliver the treatment agent to at least one selected tissue of the plant. In certain embodiments, embryo rescue techniques known in the art are used to excise an embryo from the seed prior to germination of the seed in order to better contact the embryo to the treatment agent. After excision, the embryo can be cultured in vitro or otherwise grown in conditions that promote its survival and development into a seedling. Thus, delivery of a plant treatment agent to selected tissues of a plant prior to germination can be improved using a variety of techniques currently known in the art, including embryo rescue techniques, thereby allowing the embryo to be contacted by the plant treatment agent. In certain embodiments, these methods are used to deliver a doubling agent to a meristem of a haploid embryo in order to create at least one doubled haploid reproductive tissue capable of producing functional, haploid gametes.

A monocot plant for use in methods described herein can be at any of various developmental stages. For example, maize plants can be described by their vegetative growth and reproductive stages, and as used herein, the stages of maize kernel development (Leaf Collar method: V1-Vn, Vt, R1-R6, etc.) are as described in Abendroth, L. J., R. W. Elmore, M. J. Boyer, and S. K. Marlay, 2011, Corn Growth and Development, PMR 1009, Iowa State University Extension, Ames, Iowa.

In certain embodiments, the monocot plant is a maize plant. In certain embodiments, the monocot plant is a maize plant and the plant tissue is a meristem. In certain embodiments, the monocot plant is a maize plant and the plant tissue comprises a shoot apical meristem (SAM). In certain embodiments, the monocot plant is a maize plant, the plant tissue comprises a shoot apical meristem, and the maize plant is within the seed or germinating or at or between the VE, V1, V2, V3, V4, V5, V6, V7, V8, V9, V10, V11, or V12 vegetative growth stage. In certain embodiments, the monocot plant is a haploid maize plant, the plant tissue comprises a shoot apical meristem, the maize plant is within the seed or germinating or at or between the E, V1, V2, V3, V4, V5, V6, V7, V8, V9, V10, V11, or V12 vegetative growth stage.

Methods described herein are not restricted by certain stages of a plant's development. It is anticipated that techniques of prolonging or otherwise modifying the duration of growth stages could be used in conjunction with this invention to expand a user's options of when to apply a PGR in order to induce development of additional shoot apical meristems and/or axillary buds and/or codominant ears.

Methods for Producing Doubled Haploid Plants

Certain embodiments described herein provide solutions to a problem that those of ordinary skill in the art have been struggling to solve for decades. This problem is how to ensure that substantially any doubled $DH_0$ plant will produce a desired number of $DH_1$ seeds in a single generation. In certain embodiments, the likelihood of recovering at least a minimum number of $DH_1$ seeds from a $DH_0$ plant (for example, at least one $DH_1$ seed, at least four $DH_1$ seeds, at least twenty $DH_1$ seeds, etc.) can be improved by inducing or promoting a $DH_0$ plant to develop at least one additional axillary bud. This process can be repeated with other axial buds, simultaneously and/or sequentially, until a target number of seeds is generated. By combining the seeds produced by at least one axillary bud with the seeds produced by at least one other axillary bud, and/or the seed produced by the primary bud of a $DH_0$ mother plant, these methods can improve the likelihood of recovering dozens, hundreds, or even thousands of $DH_1$ seeds from a single $DH_0$ plant.

Colchicine-based chromosome doubling protocols generally suggest exposures of several minutes to several hours and rely on the hope that during that time not only does the colchicine specifically contact cells of the shoot apical meristem that will give rise to reproductive organs, but also that the contact occurs during the specific periods of the cell cycle necessary for chromosome doubling to occur. The uncertainties of this translate into the problems of low maize doubling predictability and efficiency problems that plant breeders have been struggling to solve for many years.

In certain embodiments, the unpredictability of current DH methods can be decreased by increasing the number of chances each single mother $DH_0$ maize plant has of meeting the conditions necessary to produce a doubled-haploid inflorescence. It has been discovered that a single haploid maize plant can now be induced to produce a target number of $DH_1$ offspring with much greater frequency and reliability. Haploid plants can be induced to form multiple axillary meristems into fertile fruit-bearing structures to produce greater numbers of $DH_1$ seed as compared to control plants that have not been induced in such a manner.

Haploid monocot plants that are used for obtaining doubled haploid plants, seeds, and/or cells can be acquired by any method. In certain embodiments, haploid maize plants, or the haploid ears derived from them, can be obtained by crossing an inducer line (male) with a desired line (as female) to induce haploid plant cell formation in the female line. Exemplary inducer lines for maize include, but are not limited to, Stock 6, RWS, KEMS, Krasnodar Haploid Inducer (KHI), KMS or ZMS, lines comprising an indeterminate gametophyte (ig) mutation, and derivatives thereof. In other embodiments, wide hybridization crosses can be used to produce haploids. Exemplary descriptions of wide hybridization crosses can be found in Kasha and Kao, 1970, Nature 225:874-876. Any other method of haploid induction could also be used with these methods, including molecular or transgenic-based approaches, for example, those involving CENH3 alterations or other genome degradation-based methods.

Certain embodiments provide for methods of obtaining a doubled haploid maize plant cell, the method comprising contacting a maize plant with a solution that comprises a plant treatment agent, wherein the plant treatment agent is a chromosome doubling agent, and allowing the doubling agent to cause formation of at least one doubled-haploid plant cell. Also provided herein are methods of obtaining a doubled haploid maize plant cell, the method comprising harvesting a doubled haploid plant cell from a seed comprising a doubled-haploid plant cell. In certain embodiments, the seed is on the ear of maize as the plant cell is harvested from the seed.

Certain embodiments provide methods of obtaining a doubled-haploid maize plant, the method comprising obtaining a doubled-haploid maize embryo derived by any of the methods provided herein and supplying sufficient nutrients to the embryo to permit development of the embryo into the doubled-haploid maize plant seed. A doubled-haploid maize embryo can be formed by methods comprising performing any of the aforementioned methods of delivering a solution comprising a plant treatment agent into the shoot apical meristem, wherein the plant treatment agent is a chromosome doubling agent, and allowing the doubling agent to induce chromosome doubling.

In certain embodiments of these methods, the doubled-haploid maize plant cell is obtained from a third party. In other words, the party who caused the formation of the doubled-haploid maize plant cell is not necessarily the party who supplies the nutrients to permit development of the plant cell into the doubled-haploid maize plant.

Also provided herein are methods of obtaining a seed comprising a doubled-haploid maize plant cell, the method comprising harvesting a seed comprising a doubled-haploid plant cell obtained by the methods of obtaining a doubled-haploid maize plant cell. A doubled-haploid maize plant cell can be obtained by methods comprising performing any of the aforementioned methods of delivering a solution comprising an plant treatment agent into the plant wherein the plant treatment agent is a chromosome doubling agent, and allowing the doubling agent to induce formation of at least one doubled-haploid plant cell in at least one of the seeds. In certain embodiments, the harvested seed is a physiologically mature seed.

Also provided herein are methods of obtaining a doubled-haploid maize plant, the method comprising sowing a seed comprising a doubled-haploid maize plant cell obtained by the methods of obtaining a seed comprising a doubled-haploid maize plant cell, and permitting the sown seed to develop into the doubled-haploid maize plant. In certain embodiments, the seed comprising the doubled-haploid maize plant cell is obtained from a third party. In other words, the party who harvested the seed is not necessarily the party who sowed the seed comprising the doubled-haploid plant cell and permitted the sown seed to develop into the doubled-haploid maize plant.

In certain embodiments, doubled haploid plant cells can be obtained by harvesting $DH_1$ seed from a DH maize ear that forms on a $DH_0$ plant treated with a chromosome doubling agent by the methods provided herein. Physiologically mature $DH_1$ seed derived from the DH ear on the $DH_0$ mother plant can be harvested to obtain a doubled haploid plant cell that is contained in the seed. Physiologically mature $DH_1$ seed from the treated DH ear the $DH_0$ plant can also be sown and permitted to germinate to obtain a doubled haploid maize plant.

In certain embodiments, a haploid plant cell can be recovered from a maize ear treated with a chromosome doubling agent by rescuing a plant cell from a kernel on the ear. Plant cell rescue can be performed by removing a treated plant cell from an ear, placing the plant cell in media that provides for plant cell and/or plant development, and allowing plant cell and/or plant development to occur. In certain embodiments, media that provides for plant cell and/or plant development can include one or more phytohormones, salts, and/or sugars. Various media and techniques for plant cell rescue are described in Matthys-Rochon, et al., Journal of Experimental Botany, Vol. 49, No. 322, pp. 839-845, 1998.

These methods can be adjusted for a wide range of parameters in order to maximize nicking among the co-dominant ears of substantially any genotype of plants. One of ordinary skill in the art can adjust these methods for any number of variables known to affect plant development in conjunction with these methods, including altering planting density, dosage, chemical treatment methods or timing to improve nick and/or fertilization and/or seed production in a diverse range of plant genotypes or germplasms. In certain embodiments, plants can be planted at different densities to affect co-dominant ear formation. In certain embodiments, plants can be treated with at least one of many possible chemical agents (e.g. agents that affect ear formation like GA-inhibitors), using at least one of many possible dosage levels to optimize formation and nicking among at least two co-dominant ears in substantially any genotype or set of genotypes. In some embodiments, some other treatment known in the art to affect plant development can be provided in order to optimize co-dominant ear formation. In some embodiments, a combination of the above can be used to optimize co-dominant ear formation. In some embodiments, different treatments can be used on different genotypes in order to optimize overall co-dominant ear formation.

Plant Breeding

Methods provided herein can be used to increase the efficiency of plant breeding in monocots by increasing the number of recombinant offspring that a given mother plant produces in a single generation. This realization has dramatic and broad applications to plant breeding as it increases the likelihood that a single monocot plant will produce offspring containing a statistically unlikely yet superior combination of genetic elements. A plant breeder employing these methods to integrate certain DNA sequences, genotypes, and/or phenotypic traits into a target germplasm and/or genome will be able to create a gamete containing a sequence of DNA comprising a specific set of genetic elements using fewer mother plants and using fewer resources than a breeder using current methods known in the art. This is due, in part, to the fact that the methods described herein effectively enable a user to induce mother plants to produce more seeds per plant, which equates to more meioses per plant, which equates to more opportunities per plant for a desired genetic recombination to occur. More recombination opportunities per plant therefore translates to fewer plants (and fewer resources) needed to reach an effective population size necessary to achieve a high likelihood of recovering at least one plant with a desired combination of genetic elements.

For example, when plant breeders use recurrent selection to introgress a desired genetic element into a target germplasm, they rely on genetic recombination to occur between the homologous chromosomes of the target germplasm and the donor germplasm in loci the genomes flanking the desired genetic locus. A user of these methods will have a greater likelihood of generating a mother plant with a genome comprising the target germplasm modified only by the sequence(s) of the donor genome necessary to confer the desired genetic element because these methods generate more recombination events per mother plant, and thus a user will have a greater likelihood of creating a plant containing the desired arrangement of genetic elements incorporated into its genome than a user of other trait integration methods.

The benefits of this become even more apparent when trying to introgress multiple genetic elements into a target germplasm because the number of genetic recombination events required to introgress additional genetic elements into a target germplasm rapidly increases with the number of additional genetic elements desired to be introgressed. A user of these methods will find they need far fewer mother plants to achieve a high likelihood of recovering the desired introgression event(s), and thus, can dramatically increase the efficiency of creating a desired arrangement of genetic elements in a gamete as compared to one using current methods in the art that ignore axillary buds and/or do not deliberately induce axillary buds to produce fruit.

This realization is especially useful in inflorescent monocot species, for example maize, because each time an additional inflorescence is induced to form, an entire ear worth of potential ovules (on average 500 kernels or more for most high-yielding hybrids), each representing an opportunity for the required genetic recombinations to occur during meiosis. Thus, a breeder of ordinary skill in the art can use these methods to dramatically increase the efficiency of creating a desired arrangement of genetic elements in a gamete as compared to one using current methods in the art that ignore axillary buds or do not deliberately induce them to form and produce fruit.

These methods can be combined with any method of prolonging nick, prolonging pollen shed, or prolonging the period during which ears are receptive to pollination and fertilization that are known in the art. For example, a tassel can be subjected to a treatment that prolongs the period during which the tassel sheds pollen. T pollen that is shed can be preserved in order to extend the period of time that it is capable of successful pollination and subsequent fertilization. Other methods known to improve or extend nick can also be employed.

In certain embodiments, axillary bud induction treatments can be applied at the VE, V1, V2, V3, V4, V5, V6, V7, V8, V9, V10, V11, or V12 growth stages, or any combination thereof.

Multibuds

One type of induced axillary bud is a "multibud", which is derived by inducing a plant to form a de novo axillary bud from differentiated cells. This method effectively reprograms one or more cells of a plant to produce a de novo meristem, shoot or axillary bud.

In certain embodiments, a monocot seedling or a monocot plant embryo can be subjected to axillary bud induction while still attached to the seed (direct seed approach) or the seedling/embryo can be dissected from the seed before germination (dissected embryo method), or the seedling/embryo can be separated from the seed after germination (embryo axis method).

Disclosed herein is the discovery of several novel uses for multibuds in monocots, including the improvement of doubling efficiency ("DH"), by ensuring that a target number of seeds is generated from a cross or self. In certain embodiments, a user desiring to ensure that at least a minimum number of seeds is generated in a single generation by a $DH_0$ plant induces the $DH_0$ plant to form at least one doubled-haploid multibud. In certain embodiments, at least one of these multibuds is grown into a mature haploid plant that is selfed to produce $DH_1$ seed. This process can be repeated, simultaneously and/or sequentially, until the desired target number of seeds is generated.

In certain embodiments, these methods can first increase the number of doubled-haploid seed recovered by inducing a diploid parent plant to produce at least two diploid multibuds which are then grown into mature diploid plants. These multibud-derived parent plants can then be pollinated with an inducer to form at least one haploid seed, which can be subsequently grow into seedlings and subjected to chromosome doubling techniques known in the art to convert the haploids into a population of $DH_0$ plants. The $DH_0$ plants can then be grown until they produce flowers, and then pollinated to produce $DH_1$ seeds.

In certain embodiments, a single diploid plant can be subjected to a multibud induction treatment to generate several diploid multibuds. These multibuds can be separated from the mother plant and grown until they produce flowers, at which time they can be pollinated by an inducer. Even if some multibud-derived ears produce very few or no seeds, it is expected that this method can be repeated, either sequentially or simultaneously, until a target number of seeds are generated when all seeds from multibud-derived ears are combined. As many of these haploid plants as are necessary can be subjected to chromosome doubling to produce a desired number of DH plants.

The haploid seeds recovered and pooled from at least one multibud-induced ear can be subjected to any manner of analyses the user deems appropriate in order to determine which seeds contain specific traits. These analyses can include sorting the seeds (including the embryos and all other tissues of the seed) to identify and separate out diploid seeds, including the haploid sorting methods described in U.S. patent application Ser. No. 14/206,238 which published as US20140266196A1 and which is incorporated by reference herein in its entirety. Analyses can also include genotyping tissues using methods known in the art. Regardless of how the haploid seeds are analyzed, a subset of the population can be selected based on any criterion in order to limit the number of plants that are subjected to subsequent doubling steps. Thus, these methods can reduce the amount of resources spent doubling plants that do not meet a target selection threshold.

Unlike current methods of producing DH plants, a user of these methods does not rely on only a single chance at doubling the cells necessary to produce an ear containing at least the target number of haploid eggs. Rather, the user is able to produce multiple ears from a single $DH_0$ plant, and thus combines multiple doubling opportunities to achieve a target number of haploid eggs.

Tillers

Tillers are a type of axillary bud. The induction of tillers in monocots relaxes the suppression inhibiting the development of an axillary bud so that the axillary bud is able to form an elongated side shoot that ultimately produces a tassel and at least one female flower known as an ear. Although known to form spontaneously, the formation of tillers is an undesirable trait that is eliminated from maize breeding programs for a number of reasons, including the fact that they make preserving the identity of neighboring plants more difficult and increase the likelihood of cross-contaminating seeds of different experimental treatments. They also tend to overgrow the area normally allotted to an individual plant, which upsets planting arrangements, makes human and machine access more difficult, and disrupts efficient field maintenance, cultivation, and harvest. Furthermore, tillers compete with the mother plant (i.e. the main stem from which the tillers were derived) for nearby resources, reducing the accuracy of phenotype evaluations and overall yield per unit acre. For these and other reasons, tillers are generally eliminated from research plots and commercial operations alike.

It has been discovered, however, that by subjecting a maize plant to an axillary bud induction treatment at specific times in the plant life cycle it is possible to generate multiple tiller shoots from a single mother plant that produce ears which nick well with the tassels of the same shoot and produce excellent seed set when pollinated. Thus, these methods can increase the chance of recovering a target number of seed produced by a single maize plant by inducing it to form tillers, allowing those tillers to produce their own ears, and then harvesting the seeds from at least one of the ears produced by at least one of the tillers. By combining the seeds produced by at least one tiller with the seeds produced by at least one other tiller, and/or the seed produced by the mother plant, these methods can increase the chance of recovering dozens, hundreds, or even thousands of seeds from a single plant.

In certain embodiments, a method comprises inducing a $DH_0$ plant to form at least one doubled haploid tiller. At least one of these tillers is grown into a mature haploid plant that is selfed to produce $DH_1$ seed. The process can be repeated, simultaneously and/or sequentially, until a target number of seeds is generated. By combining the seeds produced by at least one tiller with the seeds produced by at least one other tiller, and/or the seed produced by the $DH_0$ mother plant, these methods can increase the chance of recovering of dozens, hundreds, or even thousands of seeds from a single $DH_0$ plant.

Unlike current methods of producing DH plants, these methods are not limited a single chance at doubling the cells necessary to produce an ear or tassel containing at least the target number of haploid eggs or pollen. Rather, they produce multiple ears and tassels from a single $DH_0$ plant, thus combining multiple doubling opportunities to produce an ear containing at least the target number of haploid eggs and pollen, and subsequent to pollination and fertilization, the target number of $DH_1$ seed.

Co-Dominant Ears

Certain embodiments provide for the production of co-dominant ears. In certain embodiments, the development of co-dominant ears is coordinated such that at least two co-dominant ears are receptive to pollination at a time that overlaps with pollen shed from tassels of the same plant. In certain embodiments, the development of co-dominant ears is coordinated such that at least two co-dominant ears are receptive to pollination at a time that overlaps with pollen shed from tassels of another desired germplasm.

Certain embodiments comprise subjecting a plant to an axillary bud induction treatment at specific times in a plant's life cycle. It is possible to generate at least two co-dominant ears on a single plant whose development is coordinated such that the ears nick well and produce excellent seed set when pollinated. These methods can increase the recovery of a target number of offspring seed from a single parent plant by inducing the parent plant to form multiple co-dominant ears that are all receptive to pollination in overlapping timeframes.

In certain embodiments, seeds are generated in a single generation by a $DH_0$ plant by inducing the $DH_0$ plant to form at least two co-dominant ears after doubling treatment. Unlike conventional methods of producing DH plants, these methods do not rely on only a single chance at doubling the cells necessary to produce an ear containing at least the target number of haploid eggs. Rather, multiple ears are produced from a single $DH_0$ plant, thus combining multiple doubling opportunities to produce the at least target number of haploid gametes, and subsequent to pollination and fertilization, for example to produce the target number of $DH_1$ seed.

An unexpected observation has a considerable impact on DH production. Once a $DH_0$ plant is treated with induction agent, it is not entirely predictable as to which ear on the $DH_0$ plant will produce the greatest number of $DH_1$ seed. In some cases, the second and/or third ear had better seed set than the first ear. Surprisingly, in some cases the first ear yielded few seeds or no seeds whatsoever while the second and/or third ears yielded abundant seeds.

Furthermore, representative results described herein reveal that it is stochastic as to which ear has the most doubling potential. It was demonstrated that it is not predictable which axillary meristems along the shoot are most likely to be doubled by a chromosome doubling treatment even among the closely-related members of an inbred line.

In cases where so many co-dominant ears have formed on the mother plant that there are insufficient resources to fully support their development, the ears may be cultured separately, e.g. in vitro, in separate pots, or in any other way known in the art.

In certain embodiments, the co-dominant ear induction treatment comprises applying a plant treatment agent to a plant. In certain embodiments, the plant treatment agent is a plant hormone or combination of plant hormones. In certain embodiments, the co-dominant ear induction treatment comprises applying a gibberellic acid inhibitor, such as PBZ, uniconazole, chlormequat-CL, mepiquat-CL, AMO-1618, clorphonium-Cl, tetcylacis, ancymidol, flurprimidol, paclobutrazol, uniconazole-P, inabenfide, prohexadione-CA, trinexapac-ethyl, daminozide, exo-16,17-, or dihydro-GA5-13-acetate or a combination of any plant treatment agents, for example, a GA inhibitor combination with cytokinin.

In certain embodiments, the co-dominant ears are formed on different shoots. For example, a user can treat a main stem (i.e. the mother plant) with a plant treatment agent to cause the main stem to form at least one tiller. The user times the treatment in order to coordinate the development of an ear on the tiller (i.e. a tiller ear) and an ear on the mother plant such that both ears produce silks and are receptive to pollination in a substantially-overlapping timeframe. In certain embodiments, the user treats a mother plant to form at least two tillers and times the treatments in order to coordinate the development of at least two tiller ears growing from different tillers so that the at least two tiller ears produce silks receptive to pollination during a substantially-overlapping timeframe. Thus, methods involving tillers and methods involving co-dominant ears are not mutually exclusive; it is possible to incorporate both types of axillary bud formation methods to achieve enhanced results in certain situations.

It is understood that for any of the methods disclosed herein, the method can further include selecting plants, for examples based on desired attributes such as number of tillers, number of co-dominant ears, doubling efficiency, etc.

EXAMPLES

The following examples are included to demonstrate certain embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

In the following examples, haploid maize seeds were obtained by pollinating F1 or F2 females containing desired genetics with pollen from a haploid inducer line. Ears were harvested when the seeds were mature, the ears were then shelled, and then the seeds sorted into haploid vs. diploids. Haploid maize plants used herein were obtained by pollinating F1 or F2 maize plants with pollen from a haploid inducer line to form F1 hybrid-derived haploid induction populations. Ears were harvested when the seeds were mature, shelled, and the haploid seeds recovered by standard methods of the art.

Non-limiting examples of haploid inducer lines that can be used to repeat the experiments below include Stock 6 (Coe 1959), RWS (Rober et al. 1005), KEMS (Deimling et al. 1997), KMS or ZMS (Chalyk et al. 3994; Chalyk and Chebotar 1000), or other inducer lines derived from these. The inducer line may also carry at least one marker trait to facilitate the identification of haploid offspring. The purity of the haploid pool can be made to be 95% or greater and can be verified using a variety of methods known in the art.

Example 1. Maize Ear Prolificacy can be Manipulated to Produce Multiple Ears Per Plant Across Diverse Germplasms V1-V3 seedlings of two unique F1 hybrid-derived haploid maize lines, derived from: female heterotic group (Germplasm A) or male heterotic group (Germplasm B), were subjected to a bulk colchicine-based chromosome doubling treatment by removing the seedlings from soil or growth media at the V1-V3 growth stage and aligning their stems and wrapping them together along with several wooden rods into bundle a held together by a strip of aluminum foil (approximate foil strip dimensions were 6 in×18 in). The bundled plants were submerged in plant treatment solution comprising 1250 ppm of colchicine in a centrifuge container and then the entire sample was centrifuged at 50 g for 3 min while the shoot apical meristems (SAMs) remained submerged in the plant treatment agent solution.

Following the first centrifugation, the plant treatment solution was decanted and the seedlings subjected to an addition centrifugation at 335 g for 3 min. During the second centrifugation, the rod-wrap bundle supported the seedlings and prevented the SAMs from contacting the reserve treatment agent that was not absorbed by the plant during application of the centrifugal force.

Following the second centrifugation, the plants were removed from the centrifugation container and the rod-wrap bundle and rinsed with water to remove any remaining colchicine solution, and then recovered and tended in a light, humidity, and temperature-controlled greenhouse for several days before being transplanted to a nursery greenhouse. These centrifuge-based treatment methods are described in more detail in International application number PCT/US2015/028955, which is incorporated by reference herein in its entirety, however, standard doubling treatments can also be applied to any of the haploid doubling steps referred to herein.

Following colchicine doubling treatment, 15-20 plants from each germplasm were planted in pots at two different densities; either as single plants per pot (singles), or as two plants per pot (pairs).

Next, each plant received one of two different doses of PBZ, either 50 mL (low dose) or 60 mL (high dose) of a 2.5% PBZ solution (v/v; 0.4% of active ingredient) in water. These two different doses were applied by soil drench at either the V7 or V8 growth stage, which occurred a total of 23 or 26 days after the seedlings had been subjected to chromosome doubling treatment, respectively. A control group of plants received no treatment solution but were otherwise treated exactly as the experimental groups planted as singles. When pollen shed began at the tassels, the average number of silk-producing ears (i.e. co-dominant ears) were counted for each dosage, germplasm, and treatment time and the results summarized in Table. 1.

TABLE 1

The number of co-dominant ears formed per plant in two unique induced haploid germplasms (A and B) following treatments at one of two different doses of PBZ at one of two different developmental stages following chromosome doubling treatment.

| Growth Stage† | Germplasm | Planted as Singles | | Planted as Pairs | |
| --- | --- | --- | --- | --- | --- |
| | | Low Dose | High Dose | Low Dose | High Dose |
| V7 | B | 2.7 | 3.3 | 1.5 | 1.5 |
| | A | 3.4 | 3.9 | 3 | 3.4 |
| V8 | B | 2.3 | 2.2 | 1.5 | 1.5 |
| | A | 2.3 | 3.5 | 2.3 | 2.2 |

†V7 occurred 23 days after chromosome doubling treatment; V8 occurred 26 days after chromosome doubling treatment.

The control plants for Germplasm A and Germplasm B produced 1.4 EP and 1.1 EP, respectively.

These results reveal that these methods remain useful among different planting densities. Both germplasms formed more co-dominant ears when individuals were planted singly in pots, regardless of treatment timing. All paired Germplasm B plants produced fewer ears than any of the singled Germplasm B plants, regardless of dosage or treatment timing, and the high-dose V8 Germplasm B population produced more than twice their doubled counterparts. This variance in the effect that planting density has on different germplasms provides a user with the understanding that the optimum range of planting densities that one can employ in conjunction with these methods can vary from germplasm to germplasm. It is expected that a user can adjust treatment timing and other growth or treatment conditions to optimize use of these methods with different germplasms.

These results reveal that across the variables of dosage, density, and germplasm, treatments applied at both V7 and V8 consistently produce more co-dominant ears for both germplasms than the controls. Thus, these methods are not limited to the application of co-dominant ear induction treatment during a particular point of plant development. In one embodiment, co-dominant ear induction treatment occurs at a range of times selected by the user which improve the number of seeds produced by a haploid plant treated with a chromosome doubling agent.

The results reveal that these methods are not limited to use with specific germplasms or plant genotypes. Furthermore, both germplasms showed varying improvements depending on other variables, such as planting density, treatment schedules, dosages and other variables. The number of co-dominant ears was improved for two drastically divergent genotypes over a range of different treatment schedules. It is anticipated that users will use these methods with a wide range of other germplasms and will be able to adjust parameters such as planting density, the timing of ear induction treatment(s), the dosage of chemicals used during ear induction treatment(s), and other variables that affect ear development to maximize nick among co-dominant ears and improve the number of seed produced in a given generation.

These results reveal that the use of these methods is not limited to specific dosages of chemicals that induce ear formation. A variety of different ear per plant (EP) improvements appear to correlate with dosage. For one, the average EP of all plants treated with the high dosage was 0.31 greater than the EP of all plants treated with the low dosage. This relationship is even more pronounced when only the singles were considered (the high-dose EP average was 0.55 higher than the low-dose). Furthermore, singles subjected to the low dose still produced a minimum increase of 1.2 EP over control plants, suggesting there are dosage effects even outside of the range tested here that could be used in conjunction with these methods.

Example 2. Harvesting and Pooling the Seeds of Co-Dominant Ears Improves the Recovery of $DH_1$ Seeds in a Single Generation An F1 hybrid-derived haploid induction population derived from female inbred maize plant Germplasm A was germinated in soil and tended in standard greenhouse maize growing conditions for approximately seven days. Seedlings were then subjected to a bulk colchicine-based chromosome doubling treatment as described above. Following treatment, seedlings were transplanted into pots and tended in a greenhouse at standard greenhouse maize growing conditions to recover.

Twenty-nine days after the colchicine doubling treatment, 77 of the $DH_0$ seedlings were subjected to a co-dominant ear induction treatment comprising the addition of 60 mL of 2.5% PBZ (v/v) in water, which was poured into the soil surrounding the roots of each plant. The seedlings were then tended in standard greenhouse maize growing conditions until they flowered, at which time each plant that produced pollen was self-pollinated. After approximately 3-4 weeks, ears were harvested and the kernels ($DH_1$ seeds) that formed on the treated $DH_0$ plants were counted to determine doubling efficiencies.

Doubling efficiencies (DE) were calculated under four different constraints, depending on the minimum number of kernels an ear had to produce in order to even be included in the calculation. $DE_{04}$ represents the portion of all the doubled $DH_0$ plants that produced a total of at least four seeds when all ears were considered. $DE_{20}$ represents the portion of all the doubled $DH_0$ plants that produced a total of at least 20 kernels when all ears were considered. Similarly, $DE_{30}$ represents the portion of doubled $DH_0$ plants that produced a total of at least 30 kernels when all ears were considered, and $DE_{50}$ represents the portion of doubled $DH_0$ plants that produced a total of at least 50 kernels when all ears were considered.

Furthermore, the above doubling efficiencies were calculated once by considering only the kernels that formed on the primary ear of each plant ($Ear_1$), once by considering only the kernels that formed on the primary and secondary ear of each plant ($Ear_2$), once by considering only the kernels that formed on the primary, secondary, and tertiary ear of each plant ($Ear_3$), and finally by considering all the kernels that formed on all the ears of each plant ($Ear_{all}$).

TABLE 2

Comparison of doubling efficiencies produced by co-dominant ear induction at various minimum kernel/plant thresholds. Subscripts represent the minimum number of kernels a plant had to produce in order to be considered in the calculation of DE.

|  | $DE_{04}$ | $DE_{20}$ | $DE_{30}$ | $DE_{50}$ |
|---|---|---|---|---|
| $Ear_1$ | 71% | 37% | 26% | 23% |
| $Ear_2$ | 76% | 59% | 47% | 36% |
| $Ear_3$ | 76% | 65% | 58% | 50% |
| $Ear_{All}$ | 76% | 68% | 58% | 52% |

These results reveal that greater doubling efficiencies were obtained whenever the kernels of co-dominant ears were included. This relationship becomes even more apparent when minimum yield constraints for an ear to be included were applied. For $DE_{20}$, $DE_{30}$, and $DE_{50}$, including the kernels produced by all ears on each plant approximately doubled the DE over the $EAR_1$ DE in each case. This demonstrates the utility of these methods over wide range of minimum yield constraints.

These results reveal that a user of these methods should experience more consistent DE among a variety of different minimum yield constraints as compared to methods currently known in the art. While the $Ear_1$ DE dropped by almost half between $DE_{04}$ and $DE_{20}$ (from 71% to 37%), including only one additional ear ($Ear_2$) resulted in only a 22% reduction in DE between $DE_{04}$ and $DE_{20}$ (from 76% to 59%). This reduction between $DE_{04}$ and $DE_{20}$ was even less for $Ear_3$ and $Ear_{all}$.

Since DE is a factor of the number of ears bearing a certain number of seeds recovered from an individual plant at a given generation, a user of these methods can expect to recover greater numbers of seed from a given plant, and thus will be more likely to recover at least a minimum number of seeds from any particular cross than one using methods that are presently known in the art. Thus, users of these methods will be more successful at recovering the minimum number of seeds from a cross in a single generation that is necessary to efficiently test that population to make accurate advancement decisions in a breeding program and bring products to market faster. A user of these methods will also be better able to predict DE across different minimum yield thresholds and thus will be better able to anticipate recourse allocation among the populations derived from at least one induction cross.

Example 3. The Induction of Co-Dominant Ears Improves the DE of Diverse Germplasms Two F1 hybrid-derived (one male and one female) haploid populations (referred to herein as H1 and H2) and two inbred-derived haploid lines (male Germplasm B and female Germplasm A) were tested in this experiment. Seven days after planting, several dozen seedlings from each group were removed from the soil and subjected to a bulk colchicine-based chromosome doubling treatment as described above. After the chromosome doubling treatment, seedlings were transplanted to soil and tended in a greenhouse at standard maize growing conditions. When the seedlings had reached approximately the V7 or V8 stage (approximately 29 days after doubling under the growing conditions used), the seedlings were subjected to co-dominant ear induction treatment comprising 60 mL of 2.5% PBZ added to the soil surrounding the base of each stem.

The seedlings were then tended in standard greenhouse maize growing conditions until they flowered, at which time each plant that produced pollen was self-pollinated and then left undisturbed to await fertilization and kernel production. After approximately 2-3 weeks, ears were harvested and the kernels that formed on them ($DH_1$) were counted to determine doubling efficiencies.

Doubling efficiencies (DE) were calculated under the different constraints described in the previous example to generate values for $DE_{04}$, $DE_{20}$, $DE_{30}$, and $DE_{50}$ for each of the four genotypes. Furthermore, the above doubling efficiencies were calculated once by considering only the kernels that formed on the primary ear of each plant ($Ear_1$), once by considering only the kernels that formed on the primary and secondary ear of each plant ($Ear_2$), once by considering only the kernels that formed on the primary, secondary, and tertiary ear of each plant ($Ear_3$), and finally by considering all the kernels that formed on all the ears of each plant ($Ear_{all}$).

TABLE 3

Doubling efficiencies of four germplasms depending on whether only the primary ear was harvested ($Ear_1$) or all ears were harvested ($Ear_{all}$).

|  | $Ear_1$ | | | | $Ear_{all}$ | | | |
| --- | --- | --- | --- | --- | --- | --- | --- | --- |
|  | $DE_{04}$ | $DE_{20}$ | $DE_{30}$ | $DE_{50}$ | $DE_{04}$ | $DE_{20}$ | $DE_{30}$ | $DE_{50}$ |
| Control A | 72.9 | 60.7 | 48.6 | 48.6 | 81 | 76.9 | 76.9 | 64.8 |
| A | 64.6 | 37.4 | 30.6 | 23.8 | 81.6 | 71.4 | 71.4 | 64.6 |
| Control B | 64.8 | 44.5 | 32.4 | 40.5 | 68.8 | 56.7 | 56.7 | 44.5 |
| B | 56.7 | 40.5 | 40.5 | 40.5 | 68.8 | 48.6 | 44.5 | 44.5 |

Table. 3 reveals that these methods can be used with a wide diversity of germplasms, including among inbred lines from different heterotic groups and among hybrids derived from inbreds from different heterotic groups. It also reveals that across all germplasms and minimum yield thresholds, the $Ear_{all}$ results always outperformed the $Ear_1$ results, demonstrating that a user of these methods can expect to improve DE by including the kernels produced by all additional co-dominant ears. These results suggest that these methods could be adapted for use with substantially any genotype or germplasm of maize.

Example 4. Co-Dominant Ear Induction Combines the Doubling Odds of Multiple Axillary Meristems to Improve DE and Seed Set When the $DH_1$ ears were harvested in the experiment described in Example 3, four $DH_0$ plants selected randomly from each germplasm were subjected to further scrutiny comprising recording of the approximate number of seeds produced from the first 3 co-dominant ears for each plant. FIG. 1 shows the first three ears that were harvested from each of these four plants and that figure is also represented in Table 4, below. In Table 4, ears are assigned to one of 4 categories, depending on the approximate number of seeds they produced: Class A ears produced approximately 50 seeds, Class B ears produced approximately 20-49 seeds, Class C ears produced approximately 1-20 seeds, and Class 0 ears produced zero seeds. Two plants failed to produce a third ear.

TABLE 4

Ears classified by the number of $DH_1$ seed they produced. "—" represents a situation where a third ear was not formed by the plant. The highest-yielding ear for each plant-germplasm combination is bolded in order to facilitate comparisons.

|  | Plant # | | | | | | | | | | | |
| --- | --- | --- | --- | --- | --- | --- | --- | --- | --- | --- | --- | --- |
|  | 1 | | | 2 | | | 3 | | | 4 | | |
|  | Ear # | | | | | | | | | | | |
|  | $1^{st}$ | $2^{nd}$ | $3^{rd}$ | $1^{st}$ | $2^{nd}$ | $3^{rd}$ | $1^{st}$ | $2^{nd}$ | 3 | $1^{st}$ | $2^{nd}$ | $3^{rd}$ |
| Control A | B | A | — | C | B | C | A | C | 0 | B | B | 0 |
| A | C | B | C | C | A | C | C | C | B | A | C | 0 |
| Control B | C | C | B | A | A | 0 | A | 0 | C | B | B | C |
| B | C | A | — | B | C | C | C | A | C | C | A | C |

These results reveal the discovery that different co-dominant ears have different doubling potentials. It also reveals the surprising result that the highest-yielding ears may not be the first ear, or even the first or second ear. For example, the second ear yielded the most seeds on Plant 1 from the Control A, Germplasm A and Germplasm B germplasms. For Plant 1 of Control B and Plant 3 of Germplasm A, the third ear exhibited the greatest doubling potential.

This experiment also reveals the surprising result that haploid plants subjected to a co-dominant ear induction treatment will invest more resources developing ears that have been successfully doubled and that are capable of producing viable diploid offspring, independent of the relative position of the ear on the stem. Development of haploid ears that are not doubled, and thus are unlikely to produce seed, appears to be arrested. For example, the ears producing no seed, or very few (1-4) seeds, on plant #2 and plant #3 of the H2 germplasm appear to have been arrested while the plant clearly continued to invest resources into developing the ears that did produce seed. This suggests that when development of an induced co-dominant ear growing on $DH_0$ plant is arrested it is because the ear was not doubled and not because of the ear's position on the stem. Thus, an induced co-dominant and successfully-doubled ear growing from a lower node is more likely to follow the development schedule expected of a codominant ear than an ear growing higher up the stem that is not successfully doubled.

Example 5. Co-Dominant Ear Induction Dramatically Increases Seed Production in Diploids Seeds of maize inbred lines Germplasm A and LH244 were planted in soil, germinated, and then transplanted to 10-inch pots after approximately one week, one seedling per pot. The plants were subjected to a co-dominant ear induction treatment at the V8 stage comprising drenching the soil surrounding the roots of each plant with 50 mL of a 2.5% PBZ solution (v/v; 0.4% of active ingredient). The plants were tended in a greenhouse until sexual maturity, then they were self-pollinated. When seed set had completed, the number of co-dominant ears, and the total number of kernels, produced by each plant were counted. Control plants for each germplasm were processed in the same way as the treated groups, except that the control plants were not subjected to the co-dominant ear induction treatment.

TABLE 5

Average number of ears per plant and average total kernels per plant recovered from two genotypes subjected to a co-dominant ear induction treatment vs. a control treatment.

|  | Ave. Ears Per Plant | | Ave. Total Kernels Per Plant | |
| --- | --- | --- | --- | --- |
|  | Treated | Control | Treated | Control |
| Germplasm A | 8 | 3.5 | 1677 | 746 |
| LH244 | 5.1 | 2.5 | 1126 | 557 |

Table 5 reveals the surprising result that it is possible to dramatically increase the average total kernels per plant produced from two different inbred lines by subjecting the plants to a co-dominant ear induction treatment. Both germplasms, very diverse from one another, responded to the co-dominant ear induction treatment by more than doubling the average total kernels per plant and the average ears per plant. Furthermore, all ears recorded from the treated groups in Table 5 were co-dominant.

Figure 2:
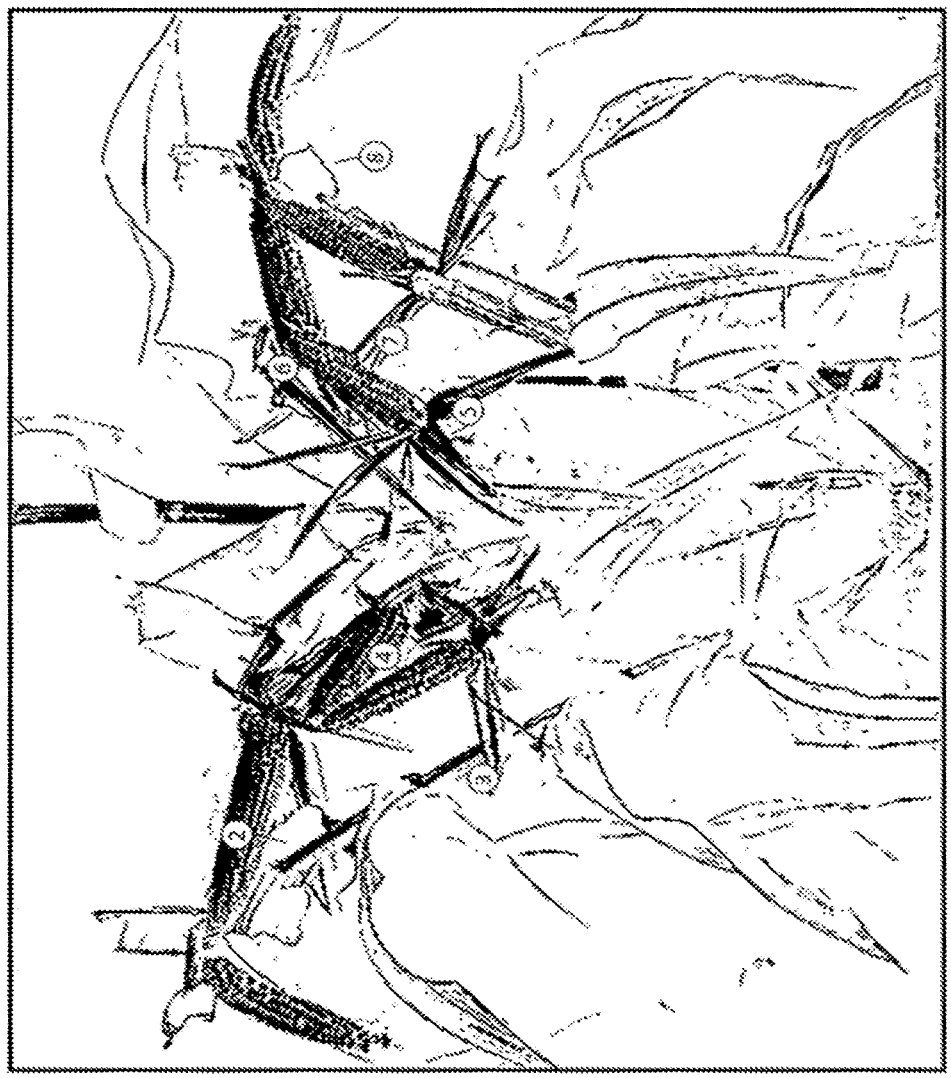
FIG. 2 shows eight numbered maize co-dominant ears growing from a single plant that was treated with a plant growth regulator.

A representative example of a Germplasm A plant that produced 8 ears following treatment with these methods is shown in FIG. 2.

Although the control plants produced multiple ears, they produced no co-dominant ears; only the primary ears on the control plants nicked well enough to produce any seed.

Example 6. Tiller Induction Dramatically Increases Seed Production in Diploids Diploid maize plants of a common inbred line were subjected to a tiller induction treatment comprising drenching the soil surrounding the roots with 100 mL of a 2.5% PBZ solution (v/v; 0.4% of active ingredient) approximately one week after germination and then allowed to grow to sexual maturity in 10-inch pots a greenhouse. A control group of plants were grown under identical circumstances except that they were not subjected to the tiller induction treatment.

Figure 3:
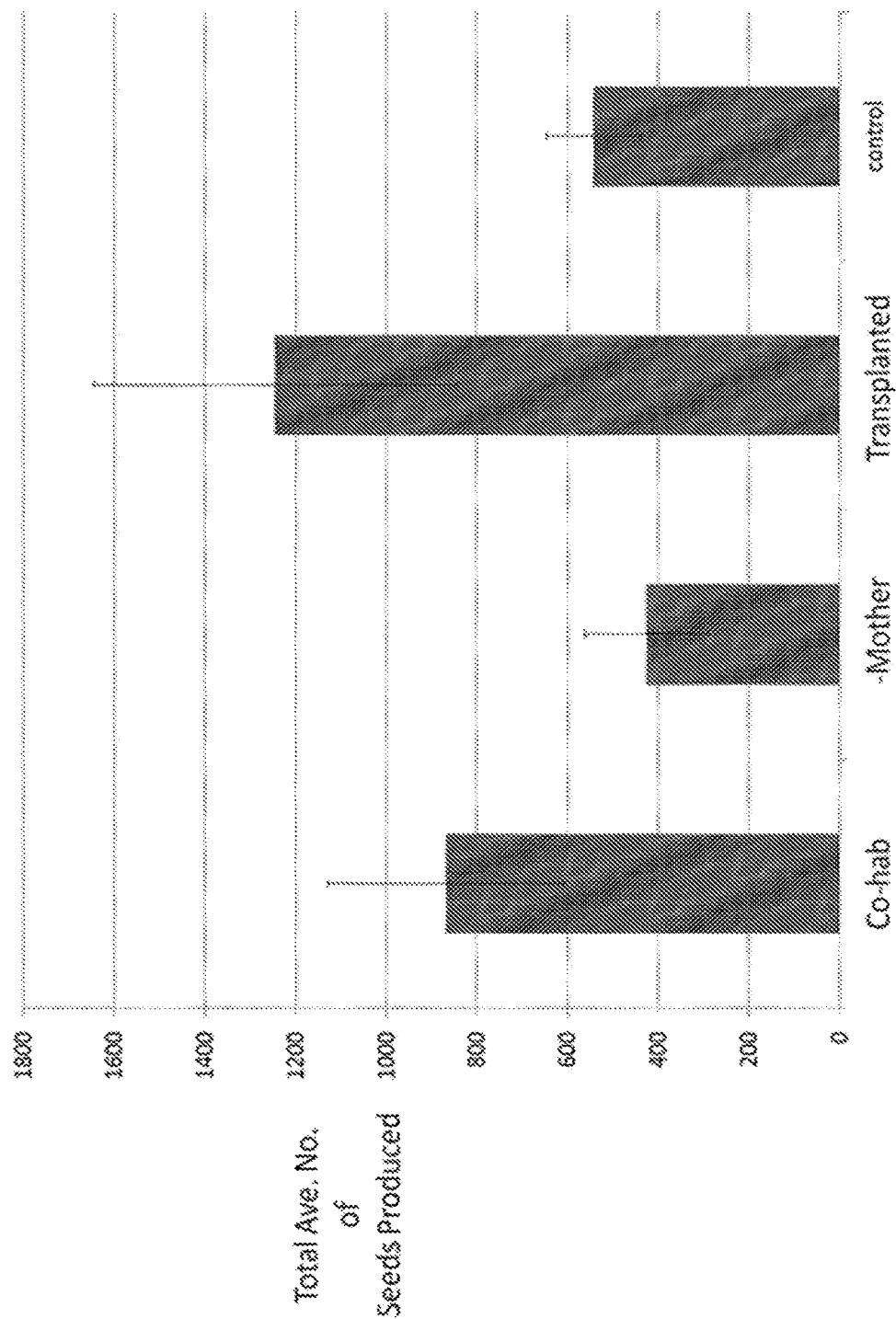
FIG. 3 shows the average total number of seeds produced from tillers derived from the same mother plant that was subjected to a tiller induction treatment.

The GA inhibitor resulted in the mother plants expressing shortened internodes, and induced the mother plants to produce tillers. Three treatment groups were then formed from the tillers: tillers of the "Co-hab" treatment were allowed to continue growing in the same pot with the mother plant; those of the "-Mother" treatment also remained in the same pot, but the mother plant was removed from the pot; and those of the "Transplanted" treatment group were transplanted from the pot containing the mother plant into separate 10-inch pots, one plant per pot. Any naturally-occurring tillers produced by the control group were allowed to grow in the same pot as the mother plant, similar to the co-hab treatment. All plants were allowed to grow to sexual maturity and self-pollinated when silks and tassels formed. When seed set was complete, the average total number of seeds produced by all plants deriving from the same mother plant seed were counted and plotted in FIG. 3.

These results reveal that it is possible to dramatically increase the average total seeds per plant by subjecting plants to a tiller-induction treatment, evidenced by the transplanted treatment group producing more than twice the number of seeds as the control group. It also reveals that the best recovery of seeds occurred when tillers were transplanted away from the mother plant.

Example 7. The Tiller-Induction Method and Doubling Haploid Plants

A haploid mother plant will be subjected to doubling treatment and thereafter planted in a pot, the soil surrounding the roots drenched with 100 mL of 2.5% of paclobutrazol, and then tended standard maize green house growing conditions for several days. The GA inhibitor will result in the mother plant expressing shortened internodes and increased tiller production. One of the resulting daughter tiller plants can be separated from the mother plant, transplanted into a separate pot, and grown via standard green house management procedures to eventually recover a daughter plant with normal haploid morphology. This daughter plant will produce abundant pollen and a robust ear that nicks well and yield several dozen $DH_1$ seeds when selfed.

It is anticipated that that these tiller induction methods can be used in conjunction with DH methods to dramatically increase the likelihood of recovering $DH_1$ seed from a given $DH_0$ mother plant. It is anticipated that a user can induce a $DH_0$ plant to form doubled-haploid tillers, each generating ears that nick well with their respective tassels to produce dozens of doubled haploid seed. It is expected that one could use these methods to generate as many tillers as are necessary to obtain a quantity of $DH_1$ seed desired by the user.

Example 8. Multibud Induction can be Used in Conjunction with DH Methods to Rapidly Generate Plants Homozygous for Multiple Traits Seeds of a diploid maize plant were surface sterilized comprising immersion using standard methods of the art and then germinated in vitro in growth media. One of the resulting seedlings was dissected from its seed two days after germination (embryo axis method). The dissected axis was then subjected to a multibud induction treatment comprising transfer to fresh multibud induction media containing cytokinin in the form of 10 mg/L BAP. After seven days in the multibud bud induction media, the treated seedlings were transferred back to a hormone-free regeneration media.

After approximately twenty days, induced multibuds could be seen growing from the nodal regions of the stem. These multibuds were dissected from the mother plant and transferred to rooting media comprising IBA and IAA. After approximately one week, the multibud-derived plants were transplanted into 10 inch pots and allowed to grow in a greenhouse until it was clear that each autonomously-growing multibud-derived shoot had formed ears and tassels that nicked. Each ear was then pollinated from the tassel growing in the same pot and then all plants were allowed to grow in greenhouse conditions until seed set. In each case, the multibud-derived plants produced ears that bore dozens of seed each.

This example reveals that multibuds induced from a single mother plant can be cultured to produce fertile ears and tassels that nick well and produce excellent seed set. It is thus anticipated that a user of these methods can use multibuds to increase the likelihood of recovering at least one seed from a given plant.

In one embodiment, the user induces a mother haploid plant subjected to chromosome doubling to a multibud induction treatment to produce multiple doubled-haploid buds. These multibuds can be cultured to produce DH seed.

In another embodiment, the user subjects a diploid plant containing at least one desired trait in a heterozygous state to a multibud induction treatment to produce several diploid multibuds. These multibuds are separated from the mother plant and grown to produce tassels and ears. Next, the user pollinates the multibud-derived diploid plants with a maternal haploid inducer to generate haploid offspring, at least one of which contains the desired allele of the trait. The haploid offspring can then be subjected to a colchicine doubling treatment to produce a doubled haploid plant containing the desired trait in the homozygous condition. This method has the potential to dramatically increase the efficiency of creating a plant that is homozygous for more than one trait as the user can induce the formation of many new inflorescences from a single mother plant, thereby increasing the likelihood of producing an egg containing the desired traits in a homozygous state from a mother plant. Once a haploid plant containing the desired traits in the homozygous condition is generated, the user can subject the plant to a chromosome doubling treatment to recover a homozygous diploid.

Example 9. Manipulation of Kernels Per Plant in Doubled Haploid Populations Using the Plant Growth Regulator Paclobutrazol Doubled Haploid seedlings were planted into soil one day after being treated with the haploid doubling agent colchicine and a total of seven days after germination. Plants of four different germplasm were treated with Paczol (2.5% in 60 mL equivalent to 0.4% active ingredient Paclobutrazol) at approximately 37 days after seed imbibition (approximately V11 stage) to form multiple co-dominant ears. All of the plants were hand pollinated for two consecutive days. Plants with co-dominant ears were hand pollinated on two separate ears on each plant (both primary and secondary ears were on the main stem). At the completion of the experiment total kernel number was determined per plant. The Table 6 below illustrates the results of untreated and treated plants in each germplasm population.

TABLE 6

Paczol treatment of Dihaploid Germplasm Populations.

| Corn DH Germplasm | Number of plants treated or untreated | Average number of kernels per plant |
|---|---|---|
| Unique Germplasm #1 | Treated, 56 | 102 |
| Unique Germplasm #1 | Not-treated, 44 | 59 |
| Unique Germplasm #2 | Treated, 56 | 63 |
| Unique Germplasm #2 | Not-treated, 44 | 35 |
| Unique Germplasm #3 | Treated, 56 | 48 |
| Unique Germplasm #3 | Not-treated, 44 | 27 |
| Unique Germplasm #4 | Treated, 56 | 49 |
| Unique Germplasm #4 | Not-treated, 44 | 28 |
| Overall counts | Treated, 224 | 66 |
|  | Not-treated, 176 | 37 |

Figure 4:
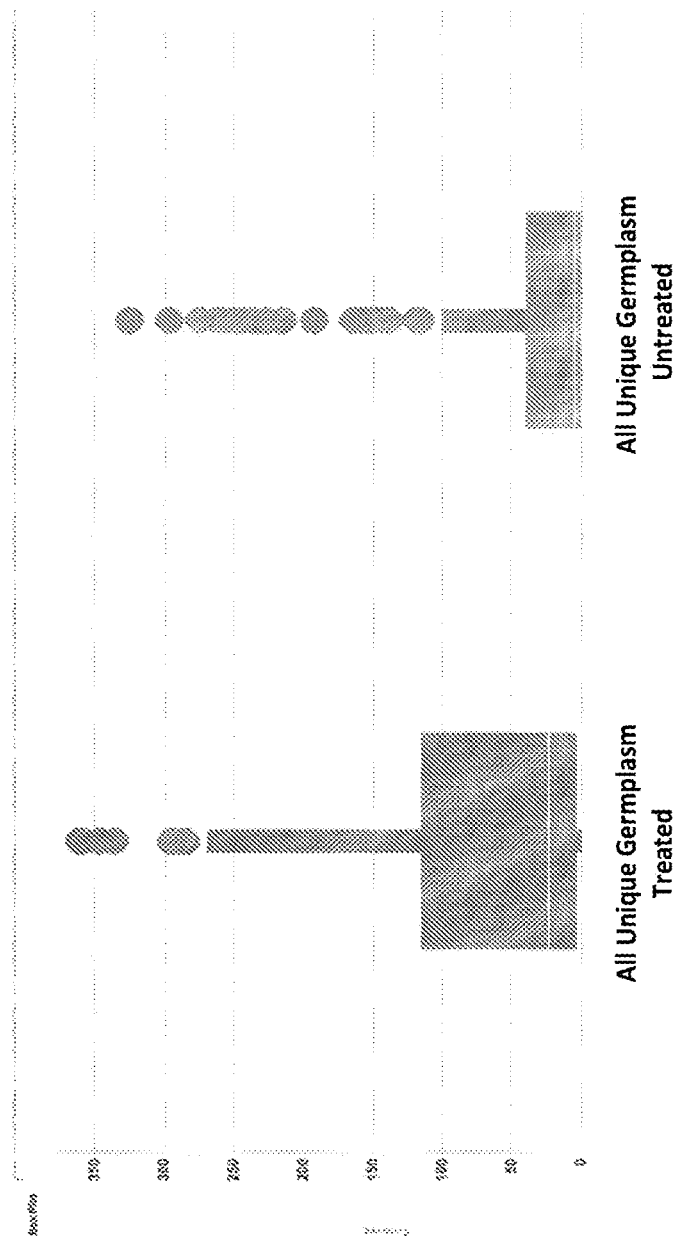
FIG. 4 shows that plants treated with PGR produced more seeds per plant.
Figure 5:
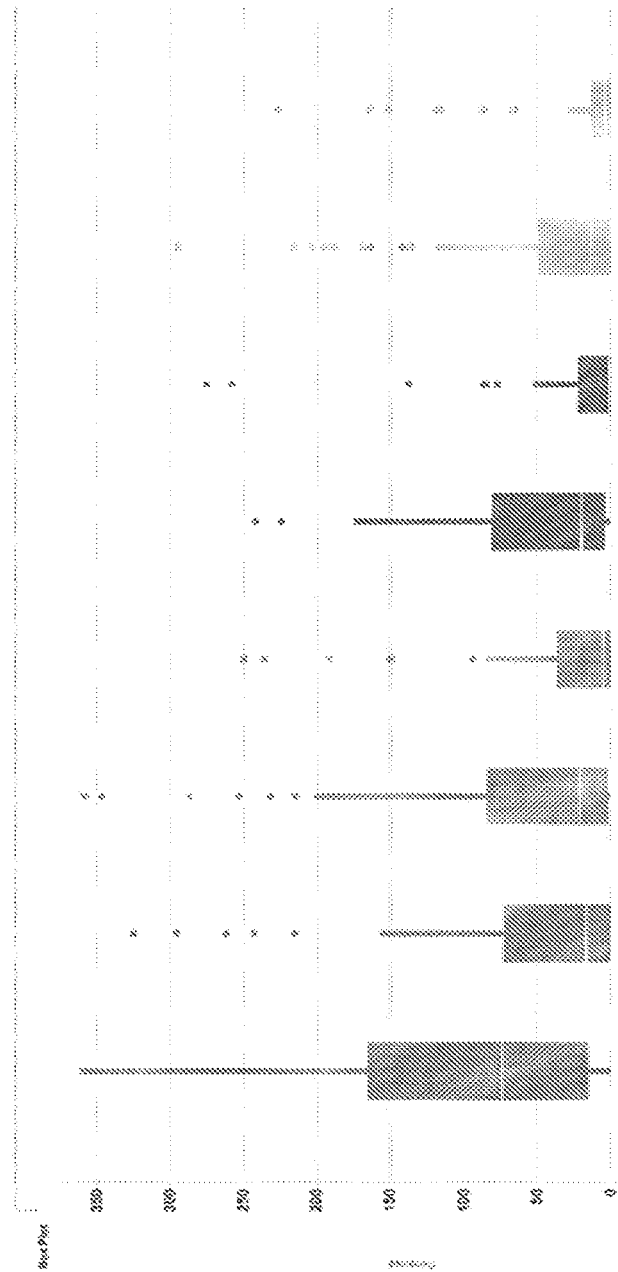
FIG. 5 shows that across lines, PGR-treated plants produced more seeds per plant.

The number of kernels per plant was nearly doubled upon treatment with Paczol. See FIGS. 4 and 5.

Having illustrated and described the principles of these methods, it should be apparent to persons skilled in the art that the methods can be modified in arrangement and detail without departing from such principles. As various modifications could be made in the constructions herein described and illustrated without departing from the scope of the invention, it is intended that all matter contained in the foregoing description or shown in the accompanying drawings shall be interpreted as illustrative rather than limiting.

Although the materials and methods disclosed herein are described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

The breadth and scope of the present disclosure should not be limited by any of the above-described exemplary embodiments, but should be defined only in accordance with the following claims and their equivalents.

What is claimed is:

1. A method of producing co-dominant ears on a haploid maize plant, the method comprising contacting the haploid maize plant with a plant growth regulator, wherein the haploid maize plant produces at least two co-dominant ears, wherein each of the at least two co-dominant ears are receptive to pollination during pollen release from the haploid maize plant,
wherein plant growth regulator is paclobutrazol.

2. A method of improving the number of $DH_1$ seeds harvested from a $DH_0$ maize plant, the method comprising contacting the $DH_0$ maize plant with a plant growth regulator at developmental stage V2, V3, V4, V5, V6, V7, V8, V9, V10, V11, or V12* and contacting the $DH_0$ maize plant with a chromosome doubling agent at any stage of its life cycle, to produce a $DH_0$ maize plant that produces at least one $DH_1$ maize seed and at least two co-dominant ears,
wherein each of the at least two co-dominant ears are receptive to pollination during pollen release from the $DH_0$ maize plant,
wherein plant growth regulator is paclobutrazol.

3. The method of claim 2, wherein the total number of $DH_1$ maize seeds produced by the $DH_0$ maize plant with at least two co-dominant ears is greater than the number of $DH_1$ maize seeds produced by control $DH_0$ maize plants that exhibit a dominant ear.

4. The method of claim 2, wherein the $DH_0$ maize plant produces a first co-dominant ear and a second co-dominant ear and the second co-dominant ear produces more DH1 maize seeds than the first co-dominant ear.

5. The method of claim 2, wherein the $DH_o$ maize plant produces a first co-dominant ear, a second co-dominant ear, and a third co-dominant ear, and the third co-dominant ear produces more $DH_1$ maize seeds than the first co-dominant ear.

6. The method of claim 2, further comprising genotyping the $DH_0$ maize plant prior to contacting the $DH_0$ maize plant with the plant growth regulator or the chromosome doubling agent.

7. The method of claim 2, further comprising obtaining $DH_1$ maize seeds from the $DH_0$ maize plant.

8. The method of claim 7, further comprising genotyping the $DH_1$ maize seeds obtained from the $DH_0$ maize plant or genotyping a plant grown from the $DH_1$ maize seeds.

9. The method of claim 8, further comprising growing a $DH_1$ maize seed selected based on the genotyping.

10. The method of claim 2, wherein the method results in a DE4 doubling efficiency of at least about 15%, results in a $DE_4$ doubling efficiency of at least about 15%, results in a $DE_{30}$ doubling efficiency of at least about 15%, and/or results in a $DE_{50}$ doubling efficiency of at least about 15%.

11. The method of claim 1, wherein the plant is contacted with the plant growth regulator by drenching, gassing, injecting, or spraying.

12. The method of claim 2, wherein the $DH_0$ maize plant is contacted with the chromosome doubling agent before it is contacted with the plant growth regulator.

13. The method of claim 2, wherein the $DH_0$ maize plant is contacted with the chromosome doubling agent after it is contacted with the plant growth regulator.

14. The method of claim 2, wherein the $DH_0$ maize plant is contacted with the chromosome doubling agent within 1 minute, 5 minutes, 15 minutes, 30 minutes, 1 hour, 2 hours, 3 hours, 6 hours, 12 hours, or 24 hours before or after contact with the plant growth regulator.

15. The method of claim 14, wherein the chromosome doubling agent and the plant growth regulator are contacted with the $DH_0$ maize plant at the same time.

16. The method of claim 1, wherein the maize plant is contacted with the plant growth regulator at developmental stage V4, VS, or V6.

17. The method of claim 1, wherein the maize plant is contacted with the plant growth regulator at developmental stage V6, V7, V8, V9, or V10.

18. The method of claim 2, wherein three or more, four or more, or five or more co-dominant ears are produced.

* * * * *

UNITED STATES PATENT AND TRADEMARK OFFICE
CERTIFICATE OF CORRECTION

Page 1 of 1

PATENT NO. : 12,108,719 B2
APPLICATION NO. : 17/218954
DATED : October 8, 2024
INVENTOR(S) : Fenggao Dong et al.

It is certified that error appears in the above-identified patent and that said Letters Patent is hereby corrected as shown below:

On the Title Page

Please delete "*" next to "Date of Patent: October 8, 2024".

Please delete "This patent is subject to a terminal disclaimer." below "Notice: Subject to any disclaimer, the term of this patent is extended or adjusted under 35 U.S.C. 154(b) by 124 days.".

Signed and Sealed this
Seventeenth Day of December, 2024

Derrick Brent
*Acting Director of the United States Patent and Trademark Office*